(12) United States Patent
Tsopanoglou et al.

(10) Patent No.: US 8,227,412 B2
(45) Date of Patent: *Jul. 24, 2012

(54) BIOACTIVE PARSTATIN PEPTIDES AND METHODS OF USE

(76) Inventors: Nikos E. Tsopanoglou, Achala (GR); Michael E. Maragoudakis, Attiki (GR)

(*) Notice: Subject to any disclaimer, the term of this patent is extended or adjusted under 35 U.S.C. 154(b) by 930 days.

This patent is subject to a terminal disclaimer.

(21) Appl. No.: 12/054,712

(22) Filed: Mar. 25, 2008

(65) Prior Publication Data

US 2008/0242613 A1    Oct. 2, 2008

Related U.S. Application Data

(60) Provisional application No. 60/908,707, filed on Mar. 29, 2007.

(51) Int. Cl.
*A61K 38/18* (2006.01)
(52) U.S. Cl. ....................... 514/13.3; 514/21.3
(58) Field of Classification Search ............... None
See application file for complete search history.

(56) References Cited

U.S. PATENT DOCUMENTS

| | | |
|---|---|---|
| 2002/0037860 A1 | 3/2002 | D'Andrea et al. |
| 2002/0045581 A1 | 4/2002 | D'Andrea et al. |
| 2002/0061852 A1 | 5/2002 | Carney |
| 2002/0103138 A1 | 8/2002 | D'Andrea et al. |
| 2002/0107204 A1 | 8/2002 | D'Andrea et al. |
| 2002/0187933 A1 | 12/2002 | Carney |
| 2003/0028008 A1 | 2/2003 | Ni et al. |
| 2003/0224999 A1 | 12/2003 | Zhang et al. |
| 2004/0063642 A1 | 4/2004 | Zhang et al. |
| 2004/0138141 A1 | 7/2004 | Zhang et al. |
| 2004/1092753 | 9/2004 | Chackalamannil et al. |
| 2005/0153884 A1 | 7/2005 | Carney |
| 2005/0158301 A1 | 7/2005 | Carney |
| 2005/0203017 A1 | 9/2005 | Hobson et al. |
| 2005/0232925 A1 | 10/2005 | Sukhatme et al. |
| 2005/0255107 A1 | 11/2005 | Kalluri |
| 2005/0267155 A1 | 12/2005 | Chelliah et al. |
| 2006/0009396 A1 | 1/2006 | Zhang et al. |
| 2006/0079684 A1 | 4/2006 | Chackalamannil et al. |
| 2006/0134167 A1 | 6/2006 | Carney |
| 2007/0202140 A1 | 8/2007 | Veltri et al. |
| 2007/0203193 A1 | 8/2007 | Thiruvengadam et al. |
| 2007/0207154 A1 | 9/2007 | Friedlander et al. |
| 2007/0232635 A1 | 10/2007 | Chelliah et al. |
| 2008/0085923 A1 | 4/2008 | Chackalamannil et al. |
| 2008/0090830 A1 | 4/2008 | Chackalamannil et al. |
| 2008/0131474 A1 | 6/2008 | Carney |

FOREIGN PATENT DOCUMENTS

WO        WO 9816548 A1 *  4/1998

OTHER PUBLICATIONS

Brady et al., "Reflections on a peptide," Nature (1994) 368:692-693.
Caunt et al., "Thrombin induces neoangiogenesis in the chick chorioallantoic membrane," J. Thromb. and Haemostasis (2003) 1:2097-2102.
Caunt et al., "Growth-Regulated Oncogene is Pivotal in Thrombin-Induced Angiogenesis," Cancer Res. (2006) 66:4125-4132.
Cheung et al., "Altered Vascular Injury Responses in Mice Deficient in Protease-Activated Receptor-1," Arterioscler. Thromb. Vasc. Biol. (1999) 19:3014-3024.
Claytor, et al., "The cleaved peptide of PAR1 is a more potent stimulant of platelet-endothelial cell adhesion than is thrombin," J. Vasc. Surg. (2003) 37:440-445.
Coughlin, "Protease-activated receptors in hemostasis, thrombosis and vascular biology," J. Thromb. Haemostasis (2005) 3:1800-1814.
Di Cera, "Thrombin Interactions," Chest (2003) 124:11S-17S.
Ferdinandy et al., "Interaction of Cardiovascular Risk Factors with Myocardial Ischemia/Reperfusion Injury, Preconditioning, and Postconditioning," Pharmacol. Rev. (2007) 59:418-458.
Furman et al., "The cleaved peptide of the thrombin receptor is a strong platelet agonist," Proc. Natl. Acad. Sci. USA (1998) 95:3082-3087.
Furman et al., "The Cleaved Peptide of PAR1 Results in a Redistribution of the Platelet Surface GPIb-IX-V Complex to the Surface-Connected Canalicular System," Thromb. Haemost. (2000) 84:897-903.
Huang et al., "Thrombin Induces Increased Expression and Secretion of VEGF from Human FS4 Fibroblasts, DU145 Prostate Cells and CHRF Megakaryocytes," Thromb. Haemost. (2001) 86:1094-1098.
Huang et al., "Thrombin induces increased expression and secretion of angiopoietin-2 from human umbilical vein endothelial cells," Blood (2002) 99:1646-1650.
Jameson et al., "A rationally designed CD4 analogue inhibits experimental allergic encephalomyelitis," Nature (1994) 368:744-746.
Kahn et al., "Protease-activated receptors 1 and 4 mediate activation of human platelets by thrombin," J. Clin. Invest. (1999) 103:879-887.
Khurana et al., "Role of Angiogenesis in Cardiovascular Disease: A Critical Appraisal," Circulation (2005) 112:1813-1824.

(Continued)

*Primary Examiner* — Christina Bradley
(74) *Attorney, Agent, or Firm* — Edwards Wildman Palmer LLP; Peter F. Corless; Richard B. Emmons

(57) ABSTRACT

Bioactive peptides that have a molecular weight of approximately 4.5 kDa and correspond to amino-terminal fragments of protease-activated receptor-1 (PAR-1), which are cleaved and released upon the proteolytic activation of PAR-1 by proteases including, but not limited to, thrombin in humans and animals are disclosed. Such synthetic or recombinantly expressed or endogenously produced or chimeric synthetic peptides that are active in vitro and in vivo and modulate endothelial cell functions and physiological and pathological processes are named herein as parstatin. Parstatin peptides, fragments, analogs, derivatives have the ability to inhibit endothelial cell growth, migration and differentiation, to induce endothelial cell apoptosis, to block angiogenesis and have cardioprotective effects in ischemia/reperfusion injury. Methods for treating angiogenesis-related diseases and endothelium dysfunction-related cardiovascular diseases are disclosed.

14 Claims, 16 Drawing Sheets

OTHER PUBLICATIONS

Leger et al., "Protease-Activated Receptors in Cardiovascular Diseases," Circulation (2006) 114:1070-1077.
Li et al., "Thrombin Induces the Release of Angiopoietin-1 from Platelets," Thromb. Haemost. (2001) 85:204-206.
Ma et al., "Proteinase-activated receptors 1 and 4 counter-regulate endostatin and VEGF release from human platelets," PNAS (2005) 102:216-220.
Mathews et al., "Crystallographic Structures of Thrombin Complexed with Thrombin Receptor Peptides: Existence of Expected and Novel Binding Modes," Biochemistry (1994) 33:3266-3279.
Mohle et al., "Constitutive production and thrombin-induced release of vascular endothelial growth factor by human megakaryocytes and platelets," Proc. Natl. Acad. Sci. USA (1997) 94:663-668.
Moser et al., "Thrombin and Vascular Development: A Sticky Subject," Arterioscler. Thromb. Vasc. Biol. (2003) 23:922-930.
Moulton et al., "Angiogenesis Inhibitors Endostatin or TNP-470 Reduce Intimal Neovascularization and Plaque Growth in Apolipoprotein E-Deficient Mice," Circulation (1999) 99:1726-1732.
Moulton et al., "Inhibition of plaque neovascularization reduces macrophage accumulation and progression of advanced atherosclerosis," PNAS (2003) 100:4736-4741.
Nelken et al., "Thrombin Receptor Expression in Normal and Atherosclerotic Human Arteries," J. Clin. Invest. (1992) 90:1614-1621.
Nierodzik et al., "Thrombin induces tumor growth, metastasis, and angiogenesis: Evidence for a thrombin-regulated dormant tumor phenotype," Cancer Cell (2006) 10:355-362.
Nyberg et al., "Endogenous Inhibitors of Angiogenesis," Cancer Res. (2005) 65:3967-3979.
Olivot et al., "Thrombomodulin Prolongs Thrombin-Induced Extracellular Signal-Regulated Kinase Phosphorylation and Nuclear Retention on Endothelial Cells," Circ. Res. (2001) 88:681-687.
Ossovskaya et al., "Protease-Activated Receptors: Contribution to Physiology and Disease," Physiol. Rev. (2004) 84:579-621.
Strande et al., "SCH 79797, a selective PAR1 antagonist, limits myocardial ischemia/reperfusion injury in rat hearts," Basic Res. Cardiol. (2007) 102:350-358.
Takada et al., "Antibody to Thrombin Receptor Inhibits Neointimal Smooth Muscle Cell Accumulation Without Causing Inhibition of Platelet Aggregation or Altering Hemostatic Parameters After Angioplasty in Rat," Circ. Res. (1998) 82:980-987.
Tsopanoglou et al., "On the Mechanism of Thrombin-induced Angiogenesis," J. Biolog. Chem. (1999) 274:23969-23976.
Tsopanoglou et al., "Role of Thrombin in Angiogenesis and Tumor Progression," Seminars in Thrombosis and Hemostasis (2004) 30:63-69.
Vu et al., "Molecular Cloning of a Functional Thrombin Receptor Reveals a Novel Proteolytic Mechanism of Receptor Activation," Cell (1991) 64:1057-1068.
Yancopoulos et al., "Vascular-specific growth factors and blood vessel formation," Nature (2000) 407:242-248.
Zucker et al., "Thrombin Induces the Activation of Progelatinase A in Vascular Endothelial Cells," J. Biol. Chem. (1995) 270:23730-23738.
GenBank Accession No. AF019616, 1999.
GenBank Accession No. AAB38308.1, 1996.
GenBank Accession No. CAA43957.1, 1996.
GenBank Accession No. P26824, 2008.
GenBank Accession No. A7YY44, 2008.
GenBank Accession No. XP_001106136, 2006.

* cited by examiner

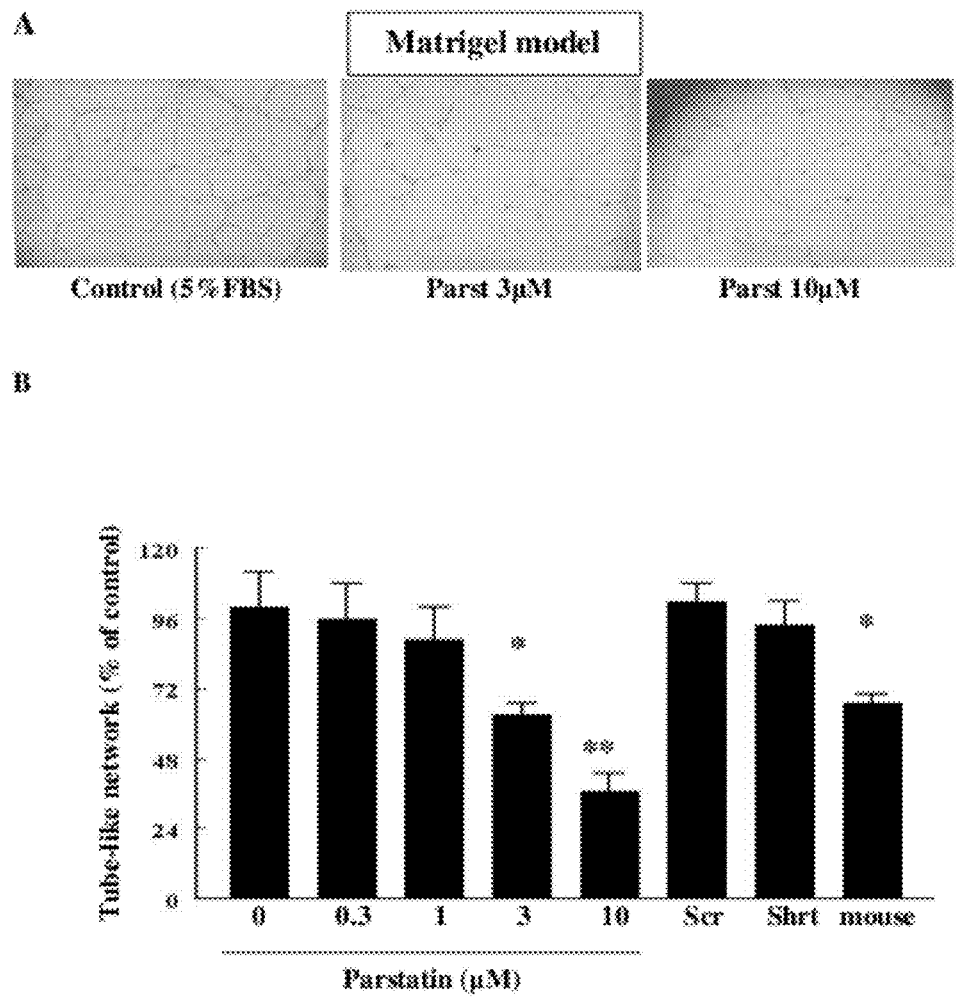

```
human     MGPRRLLLVAACFSLCGPLLSARTRARRPESKATNATLDPR  41
monkey    MGPRRLLLVAACLCLCGPLLSARTRARRPASKATNATLDPR  41
mouse     MGPRRLLIVALGLSLCGPLLSSRVPMSQFESERTDATVNPR  41
rat       MGPRRLLLVAVGLSLCGPLLSSRVPMRQFESERMYATPYAT  41
hamster   MGPQRLLLVAAGLSLCGPLLSSRVPVRQFESEMTDATVNPR  41
bovine    MGPRWLLLWAAGLGLCSPLVSARTRGPRPGTDPTNGTLGPR  41
          ***.  **.  *     .  **.**.*.*.       .*  .      .*   .
```

BIOACTIVE PARSTATIN PEPTIDES AND METHODS OF USE

CROSS REFERENCE TO RELATED APPLICATIONS

The instant application claims priority to U.S. Provisional Patent Application Ser. No. 60/908,707 filed on Mar. 29, 2007. The provisional application is incorporated herein by reference in its entirety.

SEQUENCE LISTING

A sequence listing is filed herewith to comply with the requirements of 37 C.F.R. §1.821. The sequence listing is hereby incorporated by reference.

TECHNICAL FIELD

This application relates to parstatin peptides that affect endothelial cell functions, inhibit angiogenesis, and have cardioprotective activities, and their methods of use. Parstatin is useful for treating angiogenesis-related diseases, such as angiogenesis-dependent cancer and cardiovascular diseases, such as inschemia/reperfusion injury, restenosis and pulmonary hypertension. In addition, the present invention relates to diagnostic assays and kits for assessing parstatin both in vitro and in vivo, histochemical kits for localization of parstatin in cells, molecular probes to monitor parstatin biosynthesis, and antibodies that are specific for parstatin.

BACKGROUND OF THE INVENTION

Angiogenesis is the generation of new blood vessels in a tissue or organ (Carmeliet, 2005). Under normal physiological conditions, humans and animals undergo angiogenesis only in very specific and restricted situations. For example, angiogenesis is normally observed in wound healing, fetal and embryonic development, and formation of the corpus luteum, endometrium and placenta.

Angiogenesis is controlled through a highly regulated system of angiogenic stimulators and inhibitors. The control of angiogenesis has been found to be altered in certain disease states and, in many cases, the underlying pathology associated with the diseases is related to uncontrolled angiogenesis.

Both controlled and uncontrolled angiogenesis are thought to proceed in a similar manner. Endothelial cells and pericytes, surrounded by a basement membrane, form capillary blood vessels. Angiogenesis begins with the local dissolution of the basement membrane by enzymes released by endothelial cells and leukocytes. Endothelial cells, lining the lumen of blood vessels, then protrude through the basement membrane. Angiogenic stimuli promote endothelial cell migration through the eroded basement membrane. The migrating cells form a "sprout" off the parent blood vessel where the endothelial cells undergo mitosis and proliferate. The endothelial sprouts merge with each other to form capillary loops, creating a new blood vessel.

Persistent, upregulated angiogenesis occurs in many disease states, including tumor growth metastases. The diverse pathological diseases states in which upregulated angiogenesis is present have been grouped together as angiogenic-diseases, angiogenesis-associated or angiogenesis-related diseases.

One example of diseases dependent on angiogenesis is ocular neovascular diseases (Gariano and Gardner, 2005). These diseases are characterized by invasion of new blood vessels into the structure of the eye, such as the retina or cornea. They are the most common cause of blindness and comprise approximately twenty eye diseases. In age-related macular degeneration, the associated visual problems are caused by an ingrowth of choroidal capillaries through defects in Bruch's membrane, with proliferation of fibrovascular tissue beneath the retinal pigment epithelium. Angiogenic damage is also associated with diabetic retinopathy, retinopathy of prematurity, corneal graft rejection, neovascular glaucoma, and retrolental fibroplasias. Other diseases associated with corneal neovascularization include, but are not limited to, epidemic keratoconjunctivitis, Vitamin A deficiency, contact lens overwear, atopic keratitis, superior limbic keratitis, and pterygium keratitis sicca.

Another example of angiogenesis-related disease is rheumatoid arthritis (Bainbridge et al., 2006). The blood vessels in the synovial lining of the joints undergo angiogenesis. In addition to forming new vascular networks, the endothelial cells release factors and reactive oxygen species that lead to pannus growth and cartilage destruction. Angiogenesis may also play a role in osteoarthritis. The activation of the chondrocytes by angiogenic-related factors contributes to the destruction of the joint. At a later stage, the angiogenic factors promote new bone growth. Therapeutic intervention that prevents the cartilage destruction could halt the progress of the diseases and provide relief for persons suffering from arthritis.

Chronic inflammation may also involve pathological angiogenesis. Such disease as ulcerative colitis and Crohn's disease show histological changes with the ingrowth of new blood vessels into inflamed tissue. Bartonellosis, a bacterial infection found in South America, in a chronic stage is characterized by proliferation of vascular endothelial cells.

Several lines of direct evidence now suggest that angiogenesis is essential for the growth and persistence of solid tumors and their metastases. To stimulate angiogenesis, tumors upregulate the production of a variety of angiogenic factors, including the basic fibroblast growth factor (bFGF) and vascular endothelial cell growth factor (VEGF) (Yancopoulos et al., 2000). However, many malignant tumors also generate inhibitors of angiogenesis, including angiostatin, endostastin, and thrombospondin (Nyberg et al., 2005). It is postulated that the angiogenic phenotype is the result of a net balance between these positive and negative regulators of neovascularization. Several other endogenous inhibitors of angiogenesis have been identified, although not all are associated with the presence of a tumor. These include, platelet factor 4, interferon-alpha, interferon-inducible protein 10, which is induced by interleukin-12 and/or interferon-gamma, the 16 kDa N-terminal fragment of prolactin, tumstatin, arresten, canesten, anastellin, vasostatin, and vasohibin.

Neovascularization is undoubtedly a common feature of the pathology of human atherosclerotic lesions and often is found in experimental large animals (primate, pig, and dog) models of atherosclerosis and intimal thickening (Khurana et al., 2005). The strongest experimental evidence that angiogenesis plays a causative role in atherosclerosis has come from studies in the hypercholesterolemic apolipoprotein E-deficient (ApoE−/−) mouse model (Moulton et al., 1999; 2003) In this model, endostatin, angiostatin and TNP-470, three endothelium-specific inhibitors of angiogenesis, caused a remarkable reduction of plaque area. This provides the first direct evidence that angiogenesis is involved in the process of plaque formation. Increased neovascularization has also been observed at sites of intimal hyperplasia in models of arterial stenting, angioplasty, and venous bypass graft failure.

Thrombin is a serine protease, which plays a pivotal role in haemostasis. It acts as procoagulant converting fibrinogen into fibrin that anchors platelets at the site of lesion and stabilizes the clot by activating factor XIII and enhances its own generation from prothrombin by activation of factors V, VIII and XI. On the other hand, thrombin acts as an anticoagulant by activating protein C (Di Cera, 2003).

Apart from its role in blood clotting and fibrin generation, thrombin has important roles in the initiation of angiogenesis (Tsopanoglou and Maragoudakis, 2004) Thrombin's angiogenic activity is mostly independent of its coagulant activity and is more dependent on signaling via the protease-activated receptors-1 (PAR-1). This supported by the observations obtained in mouse models, wherein a lack of thrombin generation (TF−/−, FX−/−, FV−/−, FII−/−) results in severe vascular defects in embryonic development (Moser and Patterson, 2003). Similar phenotypes occur in models of impaired thrombin binding to its PAR receptor (PAR-1−/−).

Protease-activated receptors (PARs) consists a family of G protein-coupled receptors which can be activated by proteolytic cleavage of their N-terminal extracellular domain (Ossovskaya and Bunnett, 2004). PAR-1 is the first member of this family to be cloned in which the extracellular amino terminus is cleaved to expose a new amino terminus that is involved in receptor activation (Vu et al., 1991). Subsequently, three other members of this receptor family have been identified, designated as PAR-2, PAR-3 and PAR-4. Proteolytic cleavage at the $R_{41}/S_{42}$ bond of human PAR-1 by thrombin releases a 41 amino acid peptide and unveils a tethered peptide ligand with the recognition sequence SFLLRN (SEQ ID NO:9). This sequence binds to conserved regions in the second extracellular loop of the cleaved receptor, resulting in the initiation of signal transduction. There is evidence that not only thrombin but also other molecules, such as plasmin, factor Xa, activated protein C, as well as matrix metalloprotease-1, might be able to activate this receptor under certain conditions and induce down-stream signals (Leger et al., 2006).

Thrombin, through PAR-1 signaling, interacts and stimulates a variety of vascular cells including, but is not limited to, platelets, endothelial cells, smooth muscle cells and regulates the release, expression and activation of the majority of angiogenesis mediators. For example, thrombin-induced angiogenesis in a chick chorioallontoic membrane system is associated with up-regulation of VEGF as well as angiopoietin-2 (Ang-2) (Caunt et al, 2003). Also, in endothelial cells thrombin up-regulates VEGF (Huang et al, 2001), Ang-2 (Huang et al., 2002) and the major VEGF receptor KDR (Tsopanoglou and Maragoudakis, 1999), and activates metalloproteinase-2 (Zucher et al., 1995). It was recently shown that thrombin markedly up-regulates growth-regulated oncogene-α and this chemokine in turn mediates the thrombin-induced increase of vascular regulatory proteins (MMP-1, MMP-2), growth factors (VEGF, Ang-2), and receptors (KDR) (Caunt et al, 2006). In addition thrombin induces the secretion of VEGF (Mohle et al., 1997) and Ang-1 (Li et al., 2001) from platelets. Furthermore, it was demonstrated that thrombin regulates in an opposing fashion the release of VEGF and endostatin (the potent endogenous inhibitor of angiogenesis) in platelets (Ma et al., 2005). Thrombin has also been shown to activate the proliferation of endothelial cells by acting directly as mitogenic factor (Olivot et al., 2001).

The fact that thrombin plays an important role in angiogenesis, suggests a crucial role for thrombin and its receptor, PAR-1 in tumor progression and metastasis (Nierodzik and Karpatkin, 2006). Thrombin, through PAR-1 signaling, contributes to a more malignant phenotype by activating platelet-tumor aggregation, tumor adhesion to subendothelial matrix, tumor growth and metastasis.

In addition, PAR-1 expressed on platelets and the vascular endothelium, has been shown to play important roles in normal blood vessel biology (Coughlin, 2005) and to contribute to the pathogenesis of several cardiovascular diseases including atherosclerosis, restenosis and thrombosis (Leger et al., 2006). In particular, aberrant over-expression of PAR-1 has been documented in the endothelium and vascular smooth muscle cells of human atheroscrerotic arteries, including regions of intimal thickening (Nelken et al., 1992). Activation of PAR-1 triggers mitogenic responses in smooth muscle cells and fibroblast and angiogenesis. Targeting PAR-1 with a blocking antibody reduced intimal hyperplasia by approximately 50% in a catheter-induced injury model of restenosis (Takada et al., 1998). PAR-1 deficiency also reduced restenosis in arterial injury models (Cheung et al., 1999).

Limiting infarct size by timely reperfusion is critical to improve outcomes in patients with myocardial infarction. Paradoxically, reperfusion may increase infarct size; a phenomenon known as ischemia/reperfusion injury (Ferdinandy et al., 2007). Recently, it has been shown that thrombin contributes to ischemia/reperfusion injury independently of its effects on platelets and fibrinogen. In addition, PAR-1 inhibition has been demonstrated to protect against myocardial ischemia/reperfusion injury by recruiting cardioprotective pathways (Strande et al, 2007).

Despite the wealth of information relating to the role of thrombin and PAR-1 in physiology and diseases states, the information regarding the biological role of cleaved peptides upon activation of PAR-1 is limited. There are three reports which presented evidence that correlate the 41 amino acid cleaved peptide of the PAR-1 with some platelet functions (Furman et al., 1998; 2000; 2003).

SUMMARY OF THE INVENTION

The invention includes compositions and method for prevention, amelioration, and treatment of endothelial cell growth by contacting a mammalian endothelial cell with a parstatin polypeptide. A parstatin polypeptide includes at least an active portion of the peptide of SEQ ID NO: 1, including the full-length peptide. Prevention and inhibition of endothelial cell growth can be defined by any of a number of criteria including, but not limited to, inhibition endothelial cell proliferation, inhibition of DNA synthesis, and inhibition of mitogenic intracellular biochemical pathways as compared to endothelial cells not treated with a least an active portion of SEQ ID NO: 1. Prevention and inhibition of endothelial cell growth can also include inhibition of angiogenesis which can be defined by a decrease in endothelial cell migration and/or differentiation. The invention includes prevention and/or inhibition of endothelial cell growth in culture or in an animal.

The invention further includes compositions and methods for the prevention, amelioration, and treatment of angiogenesis-related diseases. Angiogenesis-related disease include, but are not limited to, ocular diseases such as diabetic retinopathy, retinopathy of prematurity, neovascular glaucoma, macular degeneration; chronic inflammatory diseases such as arthritis, rheumatoid arthritis osteoarthritis, ulcerative colitis, Crohn's disease, psoriasis; hyperproliferative disorders such as cancer; and cardiovascular diseases such as atherosclerosis, restenosis, intimal hyperplasia, or pulmonary hypertension. The invention includes administering a parstatin polypeptide to a subject suspected of suffering from or suffering from an angiogenesis related disease in a therapeutic dose and preferably observing the subject to detect a decrease in the signs and/or symptoms of the angiogenesis-related disease.

The invention further includes compositions and method of prevention, amelioration, or treatment of ischemia/reperfusion injury in mammalian myocardium comprising contacting the myocardium with a polypeptide comprising a parstatin peptide. A parstatin polypeptide includes at least an active portion of the peptide of SEQ ID NO: 1, including the full length peptide.

The invention also includes methods to induce cell death and/or apoptosis or cell cycle arrest in mammalian endothelial cells. The invention includes contacting a mammalian endothelial cell with a parstatin peptide. A parstatin polypeptide includes at least an active portion of the peptide of SEQ ID NO: 1, including the full length peptide.

The invention also includes compositions and method for prevention, amelioration, and treatment of angiogenesis comprising contacting an angiogenesic process or sprout with a polypeptide comprising a parstatin peptide. A parstatin polypeptide includes at least an active portion of the peptide of SEQ ID NO: 1, including the full-length peptide. Inhibition of angiogenesis can be defined by a prevention and inhibition of endothelial cell growth, a decrease in endothelial cell migration and/or differentiation and/or vascular tube formation.

The invention further includes pharmaceutical compositions including a substantially purified parstatin peptide and a pharmaceutical acceptable carrier. A parstatin polypeptide includes at least an active portion of the peptide of SEQ ID NO: 1, including the full-length peptide.

Kits for testing parstatin activity and/or to detect the presence of parstatin in a sample. Kits can include antibodies targeted to parstatin peptides, including fragments of parstatin. Kits can include packaging material and/or instructions for methods of detecting parstatin in a sample.

BRIEF DESCRIPTION OF THE FIGURES

FIG. 13: Alignment of parstatin sequences from human (SEQ ID NO: 1), long-tailed dwarf hamster (SEQ ID NO: 5), mouse (SEQ ID NO: 2), rhesus monkey (SEQ ID NO: 6), rat (SEQ ID NO: 7), and cow (SEQ ID NO: 8).

DETAILED DESCRIPTION OF THE INVENTION

Figure 1:
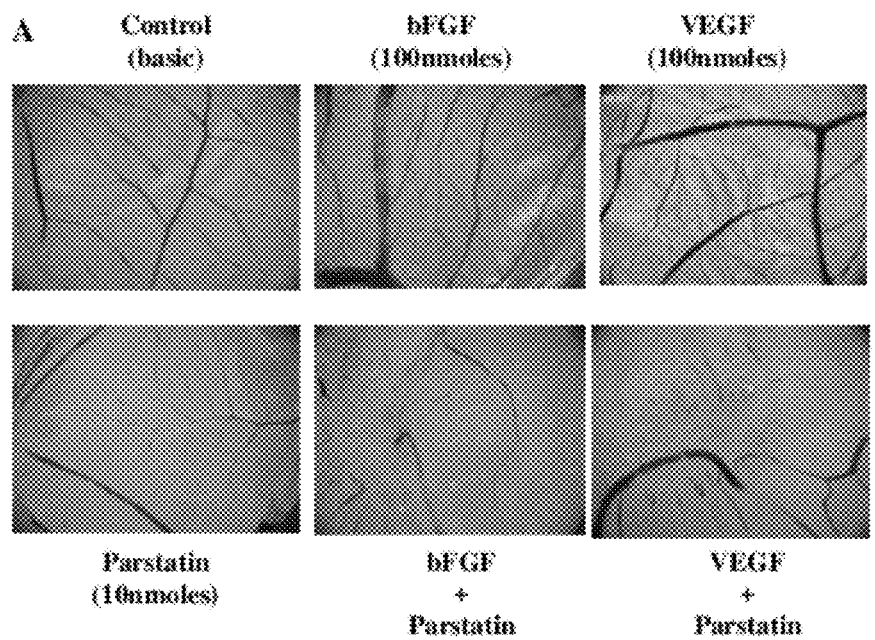
FIG. 1: Inhibition of in vivo angiogenesis in chick embryo CAM model by parstatin. (A) Angiogenesis was induced in a chick CAM model using bFGF or VEGF as indicated. Angiogeneis was inhibited using human parstatin as indicated. Representative photomicrographs are shown. (B) Quantitation of results from CAM assay. CAMs were exposed to the indicated doses of human parstatin (parst), mouse parstatin (m-parst), short parstatin (shrt-parst), scrambled parstatin (scr-parst), or growth factors (bFGF, VEGF) or the indicated combinations thereof for 48 h. The total length of vessel network was determined using image analysis software. Data are expressed as mean±SE; n=18-24; $P<0.01$
Figure 1:
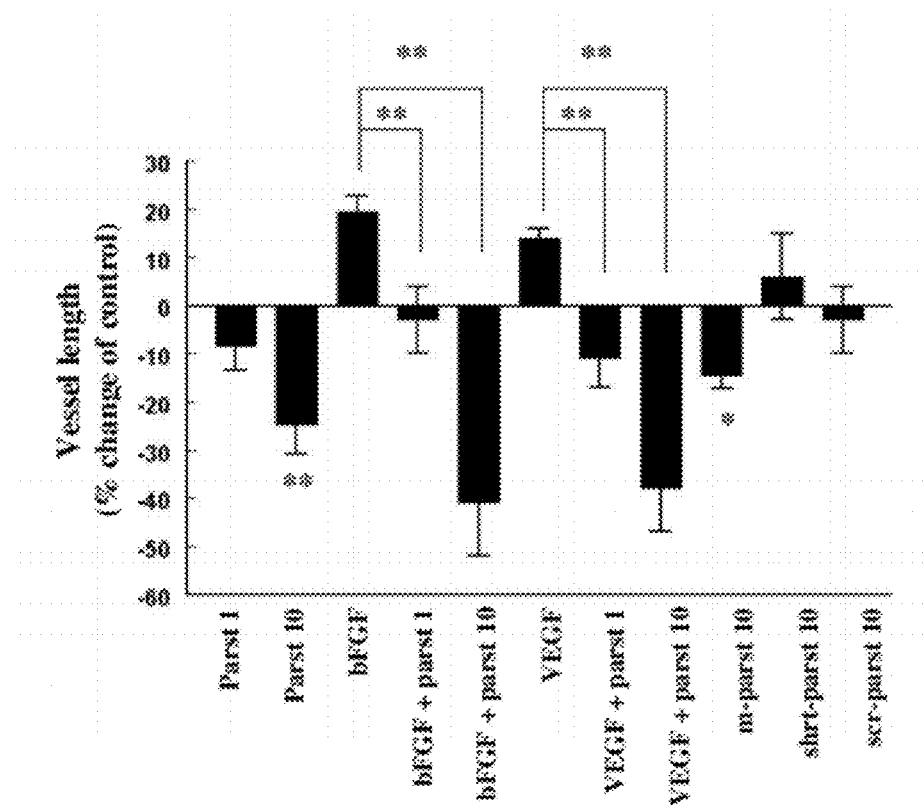

The invention includes a class of bioactive peptide molecules that have the ability to modulate endothelial cell functions and physiological and pathological processes. These peptides are collectively referred to as parstatin peptides. The invention further includes methods of use of parstatin peptides. Parstatin peptide molecules of the invention have particularly the ability to inhibit endothelial cell growth, migration, and differentiation, to induce endothelial cell apoptosis, to block angiogenesis process, and to protect against cardiovascular complications.

The term "parstatin peptide" refers to a peptide, preferably a substantially isolated or purified peptide, that is preferably about 41 amino acids and approximately 4.5 kDa in size and corresponds to cleaved peptide of human PAR-1 (Genbank Accession Number AF019616) with the sequence: MGPRRLLLVAACFSLCGPLLSARTRAR-RPESKATNATLDPR (SEQ ID NO: 1). Such peptides are naturally generated by cleavage of the N-terminal domain of the protease activated receptor-1 (PAR-1). Cleavage and release of the N-terminal domain results in the generation of a new N-terminus on the receptor, activating the receptor. Parstatin is predicted to be less than 41 residues in length because of an initial hydrophobic domain of approximately 21 to 23 amino acids (MGPRRLLLVAACFSLCGPLLSAR SEQ ID NO:10) that may represent a putative signal sequence. Indeed, PAR1 belongs to the small subgroup of G protein-coupled receptors (5-10%) possessing N-terminal signal peptides. Signal peptides have been shown to facilitate export of many secretory proteins across eukaryotic endoplasmic reticulum and are believed to be cleaved-off after mediating the endoplasmic reticulum targeting/insertion process. However, this may not always be the case. Interestingly, parstatin contains an asparagines-linked (Asn35) glycosylation site, which may prevent proteolysis of signal sequence. In addition some evidence that parstatin may released from thrombin-activated platelets has also been reported (Ramachandran et al, 1994, Thromb Haemost, 78: 1119-1124; Furman et al, 2000, Thromb Haemost, 84: 897-903).

As demonstrated herein, parstatin peptides are potent inhibitors of angiogenesis, endothelial cell growth, migration, and differentiation. As further demonstrated herein, parstatin peptides promote endothelial cell apoptosis and block the angiogenesis process. In addition, parstatin peptides have been demonstrated to be effective in the prevention and treatment of myocardial ischemia/reperfusion injury. Moreover, parstatin peptides are demonstrated to work cross species with mouse parstatin having an effect on human cells and tissues, and both mouse and human parstatin having an effect on rat cells and tissue.

The present invention is contemplated to include any derivatives of the parstatin that are active in vitro and in vivo. The present invention includes the entire parstatin peptide (full length SEQ ID NO: 1), derivatives of the parstatin peptide, and biologically-active fragments of the parstatin peptide, including truncations of the N- and/or C-terminus of SEQ ID NO: 1, and internal deletions. The term "parstatin peptides" includes longer peptides with N- and/or C-terminal extensions or insertions in the 4.5 kDa peptide of SEQ ID NO: 1, and modified peptides and proteins that have a substantially similar amino acid sequence, and which have the ability to modulate endothelial cell functions and physiological and pathological processes. The term "parstatin peptides" also includes shorter peptides with one or more amino acids is removed from either or both N- and C-terminal or from internal regions in the 4.5 kDa peptide of SEQ ID NO: 1 and modified peptides that have a substantially similar amino acid sequence, and which have the ability to modulate endothelial cell functions and physiological and pathological processes.

For example, substitutions of amino acids, wherein the replacement of an amino acid with a structurally or chemically similar amino acid does not significantly alter the structure, conformation or activity of the peptide, is well known in the art. As demonstrated herein, mouse parstatin has an effect on both human and rat cells and tissues. Human parstatin has an effect on rat cells and tissues. Sequence alignments demonstrate that human and mouse parstatin (N-terminus of Accession No. AAB38308.1, incorporated herein by reference) are 63% identical and 80% similar over the 41 amino acid length of the peptide sequences. The N-terminal 41 amino acids of the thrombin receptor of *Cricetulus longicaudatus* (long-tailed dwarf hamster, Accession No. CAA43957.1) are 68% identical and 85% similar to human parstatin. The N-terminal 41 amino acids of rat thrombin receptor (Accession No. P26824) are 67% identical and 75% similar to human parstatin over amino acids 1-37. The N-terminal 41 amino acids of the thrombin receptor of *Bos Taurus* (cow, Accession No. A7YY44) are 63% identical and 68% similar over the first 41 amino acids. The N-terminal 41 amino acids of the thrombin receptor of *Macaca mulatta* (rhesus monkey, Accession No. XP_001106136) are 92% identical and 92% similar over the first 41 amino acids. (All Accession Nos. as of the date of filing of the priority application are incorporated herein by reference.) An alignment of the sequences generated using ClustalW2 is presented in FIG. 13 and can be used to identify amino acids likely more or less tolerant to mutation. For example, mutation of amino acids conserved across all species would likely be more disruptive to function than amino acids that are not conserved across species. Such methods are well known to those of skill in the art.

Parstatin peptides having mutations or alterations that do not eliminate parstatin peptide function are also included within the scope of the invention. Such mutations or alterations can alter properties of the peptide such as bioavailability or allow for modification of the peptide with various groups. Groups may be to allow for detection of parstatin peptides (e.g., radioactive or fluorescent label) or to change or augment the activity of the peptide (e.g., a chemotherapeutic agent). Such substitutions fall within the scope of the invention. These include peptides with parstatin activity that have amino acid substitutions or have sugars or other molecules attached to amino acid functional groups. Methods for site directed mutagenesis are well known and saturation mutational analysis is a common method, especially in short peptides that can be generated by synthetic methods. Moreover, as demonstrated herein, parstatin peptides have activity across species demonstrating that sequence variation is tolerable and does not completely disrupt activity of parstatin peptides. Moreover, sites of variation between species can provide an indication of sites that can be altered while retaining function.

Parstatin peptides have at least 30%, 40%, 50%, 60%, 70%, 80%, 85%, 90%, or 95% activity as compared to the peptide of SEQ ID NO: 1 in at least one of the assays taught herein. Such assays are routine in the art. In an embodiment, the assay is in an angiogenesis assay. In an embodiment, the assay is a cell proliferation assay. In an embodiment, the assay is a cell mitogenesis assay. In an embodiment, the assay is a cell migration assay. In an embodiment, the assay is a cell differentiation assay. In an embodiment, the assay is an apoptosis assay. In an embodiment, the assay is a cell cycle progression assay. In an embodiment, the assay is a kinase activation assay. In an embodiment, the assay is an ischemia/reperfusion assay.

"Substantial sequence homology" means at least about 60% homology, at least about 70% homology, at least about 80% homology, preferably at least about 90% homology between amino acid residue sequence to the reference sequence. "Substantial sequence identity" means at least about 60% identity, at least about 70% identity, at least about 80% identity, preferably at least about 90% identity to the reference sequence.

In addition, the invention encompasses compositions in which the parstatin sequence contains a peptidomimetic. For example, the invention includes parstatin compounds in which one or more peptide bonds have been replaced with an alternative type of covalent bond, which is not susceptible to cleavage by peptidases (a "peptide mimetic" or "peptidomimetic"). Where proteolytic degradation of peptides following injection into the subject is a problem, replacement of a particularly sensitive peptide bond with a non-cleavable peptide mimetic renders the resulting peptide more stable and thus more useful as a therapeutic. Such mimetics, and methods of incorporating them into peptides, are well known in the art. Similarly, the replacement of an L-amino acid residue (e.g., with a D-amino acid) renders the peptide less sensitive to proteolysis.

Additionally, parstatin compounds of the invention can be synthesized as retro-inverso isomers, which include peptides of reverse sequence and chirality (Jameson et al., Nature, 368: 744-746, 1994; Brady et al., Nature, 368: 692-693, 1994). The net result of combining D-enantiomers and reverse synthesis is that the positions of carbonyl and amino groups in each amide bond are exchanged, while the position of the side-chain groups at each alpha carbon is preserved. For example, if the peptide model is a peptide formed of L-amino acids having the sequence ABC, the retro-inverso peptide analog formed of D-amino acids would have the sequence CBA. The procedures for synthesizing a chain of D-amino acids to form the retro-inverso peptides are known in the art.

In addition, the invention includes compositions in which the parstatin peptide or a part of it is conjugated with a "cell-penetrating moiety" or "membrane-tethering moiety". Cell-penetrating moiety is a compound which mediates transfer of a substance from an extracellular space to an intracellular compartment of a cell. Cell-penetrating moieties shuttle a linked substance (e.g., parstatin peptides, fragments, and analogs) into the cytoplasm or to the cytoplasmic space of the cell membrane. Membrane-tethering moiety is a compound which associates with or binds to a cell membrane. Thus, the membrane-tethering moiety brings the substance (e.g., parstatin peptides, fragments, and analogs) to which the membrane-tethering moiety is attached in close proximity to the membrane of a target cell. For example, a cell penetrating or membrane-tethering moiety is a hydrophobic moiety. Cell-penetrating and membrane-tethering moieties include a lipid, cholesterol, phospholipids, steroid, sphingosine, ceramide, or a fatty acid moiety. The cell-penetrating or membrane-tethering moiety is attached to the C-terminal amino acid, the N-terminal amino acid, or to an amino acid between the N-terminal and C-terminal amino acid of the parstatin or parstatin fragment.

The invention includes compositions in which the parstatin molecule, fragments, and analogs are conjugated with sugar molecules. Glycosylation is a universal characteristic of proteins in nature, which determines their physicochemical and biological properties. Design and synthesis of glycopeptides is a topic of intense research in the last years, since the carbohydrate modification can improve the pharmacokinetic characteristics, or otherwise enhance or alter the biologic activity and can be used as a tool to study the biologic functions.

Parstatin peptides of the present invention can be made by automated peptide synthesis methodologies well known to one skilled in the art. Alternatively, parstatin, of the present invention may be isolated from larger proteins, such as human PAR-1, rat PAR-1, mouse PAR-1, and primate PAR-1 proteins that share a common or similar N-terminal amino acid sequence.

Parstatin peptides can be produced upon the proteolysis of PAR-1 by proteases such as thrombin, plasmin, activated protein C, metalloprotease-1. Parstatin peptides can also be produced from recombinant sources, from genetically altered cells implanted into animals, and from platelets and cell cultures as well as other sources. It is anticipated that parstatin is made in cells of the nervous system and tumors. Parstatin can be isolated from body fluids including, but not limited to, serum, urine, and ascites, or synthesized by chemical or biological methods (e.g. cell culture, recombinant gene expression, peptide synthesis, and in vitro enzymatic catalysis of precursor molecules to yield active parstatin). Recombinant techniques include gene amplification from DNA sources using the polymerase chain reaction (PCR), and gene amplification from RNA sources using reverse transcriptase/PCR. The specific method of making the parstatin peptides of the invention is not a limitation of any of the compositions or methods of the invention.

The present invention includes methods and compositions for preventing, ameliorating, and/or treating angiogenesis related diseases, diseases having an angiogenic component, and processes mediated by undesired and uncontrolled angiogenesis by administrating to a human or animal with the undesired angiogenesis a composition comprising a substantially purified parstatin or parstatin derivatives in a dosage sufficient to prevent or inhibit angiogenesis. Parstatin peptides can be administered alone or in conjunction with other agents for the prevention, amelioration, and/or treatment of angiogenesis related diseases. The other agents can be anti-angiogenic agents. Alternatively, the agents can function to prevent, ameliorate, or treat disease by distinct methods, e.g., anti-proliferative agents for the treatment of cancer or anti-inflammatory agents for the treatment of arthritis.

The present invention provides methods and compositions for treating diseases and processes mediated endothelial cell dysfunction and cardiovascular complications by administrating to a human or animal a composition comprising a substantially purified parstatin peptide or parstatin derivatives in a therapeutically effective dose to prevent, treat, or ameliorate one or more symptoms associated with endothelium dysfunction diseases or angiogenesis, and prevent or treat conditions characterized by cardiovascular complications.

The term "angiogenesis" is understood as a physiological process involving the growth of new blood vessels from pre-existing vessels, including vasculogenesis. Vasculogenesis is the term used for spontaneous blood-vessel formation. Angiogenesis is a normal process in growth and development, as well as in wound healing. However, this is also a fundamental step in the transition of tumors from a dormant state to a malignant state. Angiogenesis is promoted by biological signals known as angiogenic growth factors that activate receptors present on endothelial cells present in pre-existing venular blood vessels. The activated endothelial cells begin to release enzymes called proteases that degrade the basement membrane in order to allow endothelial cells to escape from the original (parent) vessel walls. The endothelial cells then proliferate into the surrounding matrix and form solid sprouts or processes connecting neighboring vessels. As sprouts extend toward the source of the angiogenic stimulus, endothelial cells migrate in tandem, using integrin adhesion molecules. These sprouts then form loops to become a full-fledged vessel lumen as cells migrate to the site of angiogenesis. Sprouting occurs at a rate of several millimeters per day, and enables new vessels to grow across gaps in the vasculature.

The terms "disease" or "condition" are commonly recognized in the art and designate the presence of signs and/or symptoms in a subject or patient that are generally recognized as abnormal. Diseases or conditions may be diagnosed and categorized based on pathological changes. Signs may include any-objective evidence of a disease such as changes that are evident by physical examination of a patient or the results of diagnostic tests that may include, among others, laboratory tests to determine the presence of DNA sequence expression profiles or variant forms of certain genes in a patient. Symptoms are subjective evidence of disease or a patients condition, e.g., the patients perception of an abnormal condition that differs from normal function, sensation, or appearance, which may include, without limitations, physical disabilities, morbidity, pain, and other changes from the normal condition experienced by a subject.

The phrase "suffering from a disease or condition" means that a subject is either presently subject to the signs and symptoms, or is more likely to develop such signs and symptoms than a normal subject in the population (e.g., suffering from prostate cancer). Thus, for example, a subject suffering from a condition can include a developing fetus, a subject to a treatment or environmental condition which enhances the likelihood of developing the signs or symptoms of a condition, or a subject who is being given or will be given a treatment which increase the likelihood of the subject developing a particular condition. Thus, methods of the present invention which relate to treatments of patients (e.g., methods for selecting a treatment, selecting a patient for a treatment, and methods of treating a disease or condition in a patient) can include primary treatments directed to a presently active disease or condition, secondary treatments which are intended to cause a biological effect relevant to a primary treatment, and prophylactic treatments intended to delay, reduce, or prevent the development of a disease or condition, as well as treatments intended to cause the development of a condition different from that which would have been likely to develop in the absence of the treatment.

The term "therapy" refers to a process that is intended to produce a beneficial change in the condition of a mammal, e.g., a human, often referred to as a patient. A beneficial change can, for example, include one or more of restoration of function, reduction of symptoms, limitation or retardation of progression of a disease, disorder, or condition or prevention, limitation or retardation of deterioration of a patient's condition, disease or disorder.

The terms "drug" and "therapeutic agent," as used herein refer to a chemical entity or biological product, or combination of chemical entities or biological products, administered to a subject to treat or prevent or control a disease or condition. The drug or therapeutic agent can be formulated with one or more pharmaceutically acceptable carriers. Therapeutic agents of the instant invention, e.g., parstatin peptides, can be co-administered with other drugs or therapeutic agents. "Co-administering," as used herein refers to the administration with another agent, either at the same time, in the same composition, at alternating times, in separate compositions, or combinations thereof.

"Providing," refers to obtaining, by for example, buying or making the, e.g., polypeptide, drug, polynucleotide, probe, and the like. The material provided may be made by any known or later developed biochemical or other technique. For example, polypeptides may be obtained from cultured cells. The cultured cells, for example, may comprise an expression construct comprising a nucleic acid segment encoding the polypeptide.

Cells and/or subjects may be treated and/or contacted with one or more anti-neoplastic treatments including, surgery, chemotherapy, radiotherapy, gene therapy, immune therapy or hormonal therapy, or other therapy recommended or proscribed by self or by a health care provider.

"Obtaining" refers to purchase, procure, manufacture, or otherwise come into possession of.

As used herein, "treating, preventing or alleviating angiogenic related disease," refers to the prophylactic or therapeutic use of the therapeutic agents described herein.

"Substantially purified" when used in the context of a polypeptide or polynucleotide, or fragment or variant thereof that are at least 60% free, preferably 75% free and more preferably 90% free from other components with which they are naturally associated. An "isolated polypeptide" or "isolated polynucleotide" is, therefore, a substantially purified polypeptide or polynucleotide, respectively.

The term "subject" includes organisms which are capable of suffering from cancer or who could otherwise benefit from the administration of a compound or composition of the invention, such as human and non-human animals. Preferred human animals include human patients suffering from or prone to suffering from cancer or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc. A human subject can be referred to as a patient.

"Therapeutically effective amount," as used herein refers to an amount of an agent which is effective, upon single or multiple dose administration to the cell or subject, in prolonging the survivability of the patient with such a disorder beyond that expected in the absence of such treatment.

Compositions described herein may be administered, for example, systemically, intratumorally, intravascularally, to a resected tumor bed, orally, or by inhalation.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the expression profile or profiles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of disease or condition.

The term "effective amount" refers to a dosage or amount that is sufficient to reduce, halt, or slow tumor progression to result in alleviation, lessening or amelioration of symptoms in a patient or to achieve a desired biological outcome, e.g., slow or stop tumor growth or reduction or disappearance of a tumor. "Pharmaceutically acceptable excipients or vehicles" include, for example, water, saline, glycerol, ethanol, etc. Additionally, auxiliary substances, such as wetting or emulsifying agents, pH buffering substances, and the like, may be present in such vehicles.

The term "prevention" refers to a reduction in the chance that a subject will suffer from a particular disease or condition. The chance of a subject suffering from a particular disease or condition can be determined by a trained individual, such as a physician. For example, a subject suffering from cardiac ischemia of sufficient duration will likely suffer from reperfusion injury. Prevention can include administration of a therapeutic agent one or more times to a subject, e.g., a long standing prophylactic regimen to prevent aberrant angiogenesis, or a single dose in response to an acute event such as ischemia. Prevention can include a reduction in the level of signs or symptoms observed of the condition and need not completely eliminate all signs or symptoms of disease. Prevention can include a delay in the first onset of signs or symptoms of a disease or condition and need not prevent signs or symptoms from ever being present.

The term "amelioration" refers to a reduction of signs or symptoms of a specific disease or condition. Treatment refers to reduction of signs or symptoms of a disease or condition to reduce or eliminate signs or symptoms of the disease or condition, or to prevent progression of the disease or condition. Prevention, amelioration, and treatment need not be considered separate interventions, but instead can be considered a continuum of therapeutic interventions.

Prevention, amelioration, and or treatment of a disease is practiced on a subject first identified as being prone to or suffering from a disease or condition. During and after prevention, amelioration, and treatment of a disease or condition, a subject is typically monitored for signs or symptoms of the disease or condition.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "detectable label" is understood as a chemical modification, binding agent, or other tag that can be readily observed, preferably in a quantitative manner, such as a fluorescent tag that has a specific wavelengths of absorbtion and emission to allow detection of the compound associated with the detectable label.

The present invention also includes diagnostic methods and kits for detection and measurement of parstatin in biological fluids and tissues, and for localization of parstatin in tissues. The diagnostic method and kit can be in any configuration well known to those of ordinary skill in the art. The present invention also includes antibodies, which can be polyclonal antibodies or monoclonal antibodies, specific for the parstatin. Kits can further include packaging material and/or instructions for use of the components of the kits.

The present invention also includes oligonucleotide aptamers, which can be DNA aptamers or RNA aptamers, specific for the parstatin. The antibodies and aptamers specific for parstatin can be used in diagnostic kits to detect the presence and quantity of parstatin as index of activated PAR-1 in vivo which is diagnostic or prognostic for the occurrence or recurrence of cancer or other disease mediated by angiogenesis. Antibodies and aptamers specific for parstatin can also be administered to a human or animal against endogenous parstatin, thereby stimulating angiogenesis in situations where promotion of angiogenesis is desirable, such as in wound healing and non-healing ulcers.

The present invention also includes parstatin peptides and fragments that are labeled isotopically or with other molecules for use in the detection and visualization of parstatin binding sites with state of the art techniques, including, but not limited to, positron emission tomography, autoradiography, flow cytometry, radioreceptor binding assays, and immunohistochemistry. Such peptides and fragments can be conveniently included in kits, optionally containing instructions for use.

The parstatin peptides of the invention are useful for treating, preventing or ameliorating one or more symptoms associated with diseases and conditions characterized by aberrant angiogenic activity and/or endothelial cell dysfunction. Such diseases and conditions include, but not limited, to angiogenesis-related tumor growth and metastasis, ocular neovascular diseases, rheumatoid arthritis, chronic inflammation, ischemia/reperfusion injury, restenosis, pulmonary hypertension, atheroscherosis, intima hyperplasia. For example, such methods are carried out by contacting a cell or a tissue undergoing pathological angiogenesis with parstatin. The method involves administration to a subject, e.g., a human patient, in which such treatment or prevention is desired, a parstatin peptide in an amount sufficient to reduce the severity of the pathology in the subject, i.e., in a therapeutically effective dose. The present invention also includes pharmaceutical compositions containing any parstatin peptide and a pharmaceutically acceptable carrier.

The invention also includes nucleic acid sequences that correspond to and code for the bioactive peptide molecules of the invention, to monoclonal and polyclonal antibodies that bind specifically to such peptides molecules and DNA or RNA oligonucleotides (aptamers) that bind specifically to such peptide molecules. The biologically active peptide molecules, nucleic acid sequences corresponding to the peptides, antibodies and aptamers that bind specifically to the peptides of the present invention are useful for modulating endothelial processes in vivo, and for diagnosing and treating endothelial cell-related diseases, for example by gene therapy. Nucleic acid sequences that correspond to, and code for, parstatin and parstatin analogs can be prepared based upon the knowledge of the amino acid sequence, and the art recognized correspondence between codons, and amino acids.

Nucleic acid sequences are synthesized using automated systems well known in the art. Either the entire sequence may be synthesized or a series of smaller oligonucleotides are made and subsequently ligated together to yield the full length sequence. Alternatively, the nuclei acid sequence may be derived from a gene bank using oligonucleotides probes based on the N-terminal amino acid sequence and well known techniques for cloning genetic material.

The present invention also includes the detection of parstatin in body fluids and tissues for the purpose of diagnosis or prognosis of angiogenesis-mediated diseases such as cancer, cardiovascular diseases, ocular diseases, and arthritis. Antibodies and aptamers that specifically bind to the parstatin can be used in diagnostic methods and kits that are well known to those of ordinary skill in the art to detect or quantify the parstatin in a body fluid or tissue. Results from these tests can be used to diagnose or predict the occurrence or reccurrence of a cancer and other angiogenesis mediated diseases and pathophysiological processes wherein PAR-1 is involved.

The present invention further includes the detection of parstatin binding sites and receptors in cells and tissues. The present invention also includes methods of treating or preventing angiogenic diseases and processes including, but not limited to, arthritis, diabetic retinopathy and tumors by stimulating the production of parstatin, and/or by administrating substantially purified parstatin polypeptides, parstatin agonists, or parstatin antagonists. It is to be understood that the parstatin can be of animal, particularly mammalian, for example of human in origin. Parstatin can also be produced synthetically by chemical reaction or by recombinant techniques in conjunction with expression systems. Parstatin can also be produced by enzymatically cleaving different molecules, including parstatin precursors or peptides, containing sequence homology or identity with segments of parstatin to generate peptides having anti-angiogenesic activity.

Passive antibody therapy using antibodies that specifically bind parstatin can be employed to modulate endothelial-dependent processes such as reproduction, development, and wound healing and tissue repair. Antibodies specific for parstatin, parstatin peptides, and parstatin analogs are made according to techniques and protocols well known in the art. The antibodies may be either polyclonal or monoclonal. The antibodies are utilized in well know immunoassay formats, such as competitive and non-competitive immunoassays, including ELISA, sandwich immunoassays, and radioimmunoassay (RIAs), to determine the presence or absence of the endothelial proliferation inhibitors of the present invention in body fluids. Examples of body fluids include but are not limited to blood, serum, peritoneal fluid, pleural fluid, cerebrospinal fluid, uterine fluid, saliva and mucus.

Oligonucleotides therapy using aptamers that specifically bind parstatin can be employed to modulate endothelial-dependent processes such as reproduction, development, wound healing, and tissue repair. The term "aptamers" refers to nucleic acid molecules (DNA or RNA) having specific binding affinity to molecules through interactions other than classic Watson-Crick base pairing. Aptamers, like peptides generated by phage display or monoclonal antibodies are capable of specifically binding to selected targets and modulating the target's activity or binding interactions, e.g., through binding aptamers may block their target's ability to function. Aptamers specific for parstatin and parstatin analogs are made according to techniques and protocols well known in the art. A typical aptamer is 10-15 kDa in size (20-45 nucleotides), binds its target with nanomolar to subnanomolar affinity, and discriminates against closely related targets.

The peptides, nucleic acid sequences, antibodies, and aptamers of the present invention are useful for diagnosing and treating endothelial cell-related diseases and disorders. A particularly important endothelial cell process is angiogenesis, the formation of blood vessels. Angiogenesis-related diseases may be diagnosed and treated using the endothelial cell proliferation inhibiting proteins of the present invention, i.e., parstatin peptides and analogs. Angiogenesis-related diseases include, but are not limited to, angiogenesis-dependent cancer (solid tumors, blood born tumors such as leukemias, ands tumor metastases; benign tumors, for example hemangiomas, acoustic neuromas, neurofibromas), rheumatoid arthritis, psoriasis, ocular angiogenic diseases (diabetic retinopathy, petinopathy of prematurity, macular degeneration, corneal graft rejection, neovascular glaucoma, retrolental fibroplasias), myocardial angiogenesis, plaque neovascularization, and wound granulation.

The parstatin endothelial cell proliferation inhibiting peptides of the present invention are useful in the treatment of disease of excessive or abnormal stimulation of endothelial cells. These diseases include, but are not limited to, intestinal adhesions, atherosclerosis, scleroderma and hypertrophic scars, i.e., keloids. They are also useful in the treatment of diseases that have angiogenesis as a pathologic consequence such as cat scratch disease (Rochele minalia quintosa) and ulcers (*Helobacter pylori*).

Conversely, blockade of parstatin receptors with parstatin analogs which act as receptor antagonists as well as blockade of parstatin molecules with antibodies or aptamers, which specifically bind and inhibit parstatin biological activity, may promote endothelialization and vascularization. Such effects may be desirable in situations of inadequate vascularization of the uterine endometrium and associated infertility, wound repair, healing of cuts and incisions, treatment of vascular problems in diabetics, especially retinal and peripheral vessel, peripheral angiopathies, especially peripheral ischemic vascular disorders, promotion of vascularization in transplanted tissue including muscle and skin, promotion of vascularization of cardiac muscle especially following transplantation of a heart or heart tissue and after bypass surgery, promotion of vascularization of solid and relatively avascular tumors for enhanced cytotoxin delivery, and enhancement of blood flow to the nervous system, including but not limited to the cerebral cortex and spinal cord.

The amino acid sequence of the peptide is known and the parstatin can be synthesized by technique well known in the art, as exemplified by "Solid Phase Peptide Synthesis: A Practical Approach" E. Atherton and R. C. Sheppard, IRL Press, Oxford, England. Similarly, multiple fragments can be synthesized which are subsequently linked together to form larger fragments. These synthesis peptide fragments can also be made with amino acid substitutions at specific locations in order to test for agonistic and antagonistic activity in vitro and in vivo. Peptide fragments that possess high affinity binding to tissues can be used to isolate the parstatin receptor on affinity columns. Isolation and purification of the parstatin receptor is a fundamental step towards elucidating the mechanism of action of parstatin. This facilitates development of drugs to modulate the activity of the parstatin receptor, the final pathway to biological activity. Isolation of the receptor enables the construction of nucleotide probes to monitor the location and synthesis of the receptor, using in situ and solution hybridization technology.

The synthetic peptide fragments of parstatin have a variety of uses. The peptide that binds to the parstatin receptor with high specificity and avidity can be detectably labeled, e.g., radiolabeled or fluorescently labeled, and employed for visualization and quantitation of binding sites using known techniquese, such as membrane binding techniques. This application provides important diagnosis and research tools. Knowledge of the binding properties of the parstatin receptor facilitates investigation of the transduction mechanisms linked to the receptor. In addition, labeling these peptides with short lived isotopes enables visualization of receptor binding sites in vivo using positron emission tomography or other modern radiographic techniques in order to locate tumors or cardiovascular complications with parstatin binding sites.

Systematic substitution of amino acids within parstatin or its fragments yields high affinity peptide agonists and antagonists to the parstatin receptor that enhance or diminish parstatin binding to its receptor. Such agonists are used to suppress the growth of micrometastases, thereby limiting the spread of cancer. Antagonists to parstatin are applied in situations of inadequate vascularization, to block the inhibitory effects of parstatin and possibly promote angiogenesis. This treatment may have therapeutic effects to promote wound healing in diabetics.

According to the present invention, parstatin can be used in combination with other compositions and procedures for the treatment of diseases. For example, a tumor may be treated conventionally with surgery, radiation, and/or chemotherapy combined with parstatin and then parstatin may be subsequently administered to the patient to extend the dormancy of micrometastases and/or to stabilize any residual primary tumor.

The peptides and peptides fragments with the parstatin activity described above can be provided as isolated and substantially purified peptides and peptides fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal, or parenteral (e.g., intravenous, intraspinal, subcutaneous, or intramuscular) route. In addition, the parstatin may be incorporated into biodegradable polymers allowing for sustained release of compound, the polymers being implanted in the vicinity of where drug delivery is desired, for example, at the site of a tumor or implanted so that the parstatin is slowly released systemically. Osmotic minipumps may also be used to provide controlled delivery of high concentrations of parstatin through cannulae to the site of interest, e.g., directly into a metastatic growth or into the vascular supply to that tumor.

Cytotoxic and antiangiogenic compounds are used in medical devices, e.g., as drug eluting stents to prevent restenosis and intimal hyperplasia. For example, a vascular endoprosthetic device, e.g., a stent includes parstatin. The composition is impregnated in the device or the device is coated with the parstatin.

The dosage of the parstatin of the present invention will depend on the disease state or condition being treated and other clinical factors such as weight and condition of the human or animal and the route of administration of the compound. For treating humans or animals, between approximately 0.5 mg/kilogram to 500 mg/kilogram of the parstatin can be administered. A more preferable range is 1 mg/kilogram to 100 mg/kilogram with the most preferable range being from 1 mg/kilogram to 50 mg/kilogram. Depending upon the half-life of the parstatin in the particular animal or human, the parstatin can be administered between several times per day to once a week. It is to be understood that the present invention has application for both human and veterinary use. The methods of the present invention contemplate single as well as multiple administrations, given either simultaneously or over an extended period of time.

Formulations suitable for parenteral administration include aqueous and non-aqueous sterile injection solutions which may contain anti-oxidants, buffers, bacteriostatics and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references, patents, patent applications, and Accession Numbers as of the filing date of the priority application referred to herein are specifically incorporated by reference.

The invention is further illustrated by the following examples, which are not meant to be construed in any as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Peptides Synthesis and Compositions

All peptides used in the experiments described herein were synthesized in the core peptide facility of Peptide Specialty Laboratories GmbH (Heidelberg, Germany), Ezbiolab Inc. (Westfield, Ind., USA) and Biosynthesis, Inc. (Lewisville, Tex., USA). Synthesized peptides were purified by HPLC technology, were characterized by mass spectrometry technology and were sequenced. The synthesized peptides were as follow:
1. Human parstatin, which corresponds to 1-41-amino acids cleaved N-terminal fragment of human PAR-1. Sequence: MGPRRLLLVAACF-SLCGPLLSAR-TRARRPESKATNATLDPR (SEQ ID NO: 1) (molecular weight of 4468 Da).
2. Human parstatin conjugated with fluorescent isothiocyanate (FITC, fluorescein). Sequence: FITC-Ahx-MG-PRRLLLVAACFSLCGPLLSAR-TRARRPESKAT-NATLDPR (SEQ ID NO: 1) (molecular weight of 4968 Da).
3. Mouse parstatin, which corresponds to 1-41-amino acids cleaved N-terminal fragment of mouse PAR-1. Sequence: MGPRRLLIVALGLSL-CGPLLSSRVPM-SQPESERTDATVNPR (SEQ ID NO: 2) (molecular weight of 4420 Da).
4. Scrambled human parstatin, which contains to randomly rearranging the amino acid sequence to human parstatin. Sequence: LRTNASLLVPFLT-ARAKSSGTREAADP-PRLMCLRPLARRCG (SEQ ID NO: 3) (molecular weight of 4468 Da).
5. Human short parstatin, which corresponds to 24-41 (18 amino acids) amino acid sequence of human parstatin.

Sequence: TRARRPESKATNATLDPR (SEQ ID NO: 4) (molecular weight of 2041 Da).
6.

Example 2

Parstatin Inhibits Angiogenesis In Vivo

The in vivo chick chorioallontoic membrane (CAM) angiogenesis model was used to evaluate the effect of parstatin in angiogenesis. On incubation day 9 of fertilized chicken eggs, an O-ring (1 cm$^2$) was placed on the surface of the CAM and the vehicle or the indicated substances were placed inside this restricted area. After 48 h, CAMs were fixed in saline-buffered formalin, photographed, and analyzed using the Scion Image software (Scion Image Release Beta 4.0.2 software; Scion Corporation, Frederick, Md.). Image analysis was performed on at least 18 eggs for each group. Vessel number and length were evaluated by pixel counting, and the results expressed as mean percentage of control±SE. Statistical analyses were performed using a Student's t test.

As shown in FIGS. 1A and B, parstatin was very potent antiangiogenic substance. The application of human parstatin on CAM of chick embryo, at concentration of 10 nmoles, resulted in a significant inhibition of the basal level of angiogenesis that occurs in CAMs. This inhibitory effect was dose-dependent and not toxic for the chick embryo, at concentrations up to 300 nmoles. Interestingly, the anti-angiogenic effect of parstatin was more pronounced when angiogenesis was stimulated by growth factors such as bFGF or VEGF.

Mouse parstatin also inhibited vessel formation on CAM model but to lesser extent as compared to human parstatin. These data demonstrate that parstatin peptides are capable of working across species (i.e., human and mouse on chicken) and that some sequence variation is tolerable while retaining activity of the parstatin peptides as antiangiogenic agents. The application of short and scrambled parstatins, at concentration similar to that of human or mouse parstatins (10 nmoles), did not cause any significant effect. These results demonstrate the sequence specific, dose specific effect of both human and mouse parstatin peptides on vascular growth in an accepted angiogenesis model.

Example 3

Parstatin Inhibits Angiogenesis in Rat Aortic Ring Assay

The recognition that angiogenesis in vivo involves not only endothelial cells but also their surrounding cells, has led to development of angiogenic assays using organ culture methods. Of these, the rat aortic ring assay has become the most widely used.

Freshly cut aortic rings obtained from 5- to 10-week-old Fischer 344 male rats were embedded in collagen gels and transferred to 16-mm wells (4-well NUNC dishes) each containing 0.5 ml serum-free endothelial basal medium (EBM, Clonetics Corporation) alone or supplemented with VEGF or bFGF. The angiogenic response of aortic cultures was measured in the live cultures by counting the number of neovessels over time using art accepted methods. Results expressed as mean number of microvessels±SE. Statistical analysis was performed using unpaired two-tailed t-test.

Figure 2:
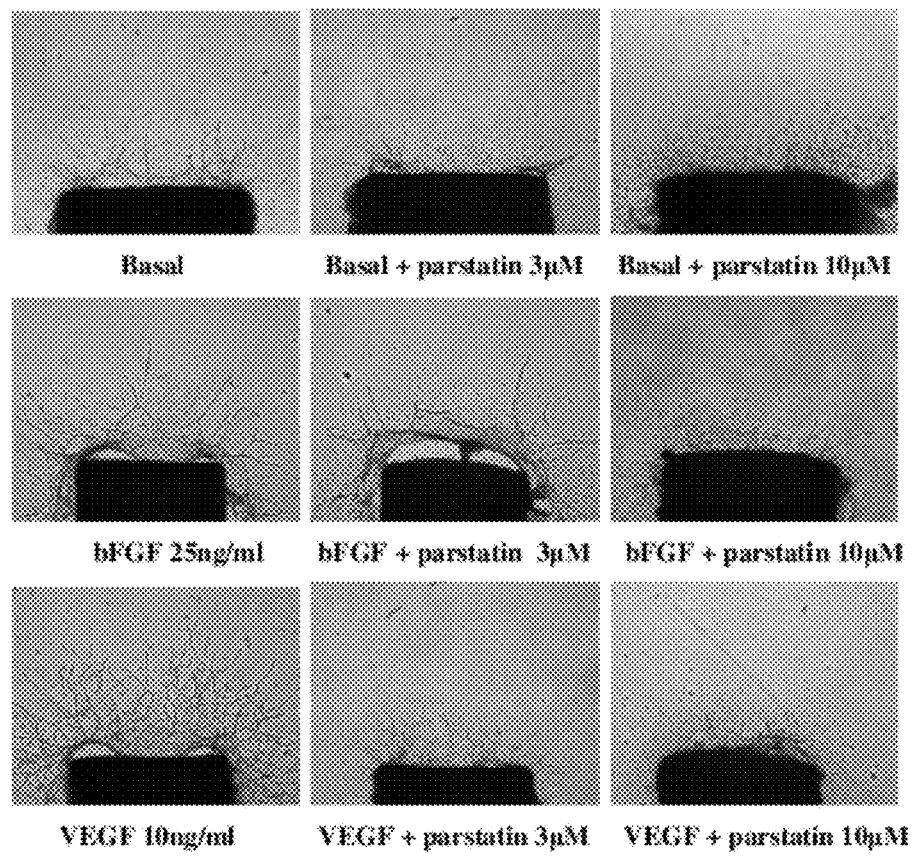
FIG. 2: Inhibition of ex vivo angiogenesis in rat aortic rings by parstatin. (A) Collagen embedded freshly cut rat aortic rings were incubated either in basal growth medium or in medium supplemented with VEGF or bFGF for 7 days as indicated. Cultured rings were exposed in vehicle alone or in indicated concentrations of human parstatin (parst). Representative photomicrographs are shown. (B) Quantitation of aortic ring angiogenesis. Angiogenesis was estimated by counting the number of neovessels at the end of experiments. Data are expressed as mean±SE; n=6 rings/group; $P<0.01$
Figure 2:
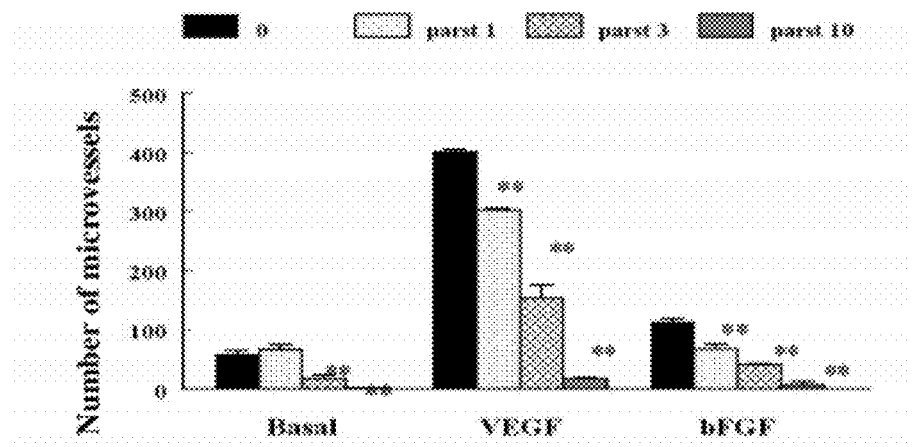

As shown in FIGS. 2A and B, parstatin inhibits microvessel formation in a dose-dependant manner, with complete inhibition at a 10 mM. This inhibitory effect was evident either in basal conditions or in VEGF- or bFGF-induced angiogenesis. Again, the ability of parstatin to function across species is noted. Human parstatin effectively inhibits angiogenesis in rat tissue in a non-species specific, dose dependent manner.

Example 4

Parstatin Inhibits Capillary Tube-Like Formation by Endothelial Cells

Primary human umbilical vein endothelial cells (HUVEC cells) were obtained from freshly delivered umbilical cords from caesarean births and were grown in M199 medium with 20% fetal bovine serum (FBS) supplemented with endothelial cell growth supplement and heparin. One of the most specific tests for angiogenesis is the measurement of the ability of endothelial cells to form capillary-like structures (i.e., tube formation). Tube formation is a multi-step process involving cell adhesion, migration and differentiation. Tube formation can be enhanced by use of Matrigel or fibrin clots to coat plastic culture dishes and it is an accepted model of angiogenesis.

Matrigel™ (Becton Dickinson Labware, N.J., USA) is a mixture of basement membrane components extracted from the Englebreth-Holm-Swarm tumor. It has been demonstrated that endothelial cells attach, migrate, and assemble to form tube-like structure resembling capillaries within 18 hours of plating. Matrigel™ (250 µl) was added to each well of a 24-well plate and allowed to polymerize. A suspension of 40,000 HUVEC cells in M199 medium containing 5% FBS was added into each well coated with Matrigel™.

Figure 3:
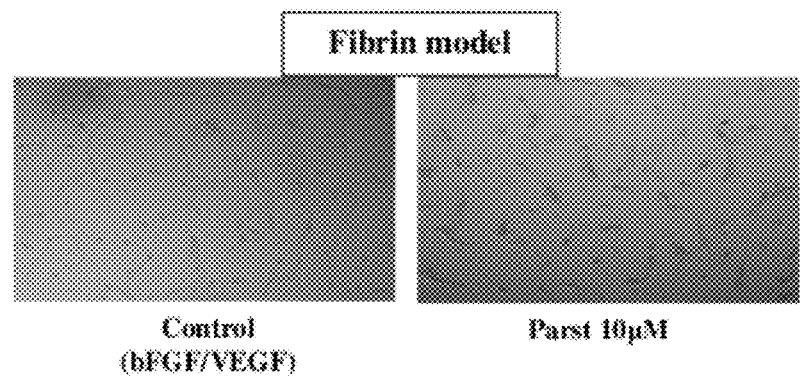
FIG. 3: Inhibition of endothelial cell angiogenesis-related activity by parstatin. (A) Representative photomicrographs of a tube formation angiogeneisis assay of HUVEC cells plated onto Matrigel layers in the presence of 5% FBS and exposed to indicated concentrations of parstatin peptide are shown. (B) Quantitation of an angiogenesis assay in which HUVEC cells were plated onto Matrigel layers with medium containing 5% serum (FBS), in the absence (control) or in the presence of indicated concentrations of human parstatin (parst), mouse parstatin (m-parst, 10 μM), short parstatin (shrt-parst, 10 μM), or scrambled parstatin (scr-parst, 10 μM). The formed network was fixed after 18 hours, stained and quantitated in triplicate at least twice using image analysis software. Data are expressed as mean±SE; *$P<0.05$, **$P<0.01$ (C): Inhibition of tube formation (three dimensions) within fibrin in vitro angiogenesis model. HUVEC cells were cultured between two fibrin layers in medium containing growth factors (VEGF/bFGF, 25 ng/ml each) with or without human parstatin. Representative photomicrographs are shown. (D) Quantitation of a fibrin angiogensis assay. HUVEC cells were grown in the presence of VEGF/bFGF in the absence (control) or in the presence of indicated concentrations of human parstatin (parst), mouse parstatin (m-parst, 10 μM), short parstatin (shrt-parst, 10 μM), or scrambled parstatin (scr-parst, 10 μM). The formed capillary-like network was fixed after 24 hours, stained and quantitated in triplicate at least twice using image analysis software. Data are expressed as mean±SE; *$P<0.05$, **$P<0.01$ (E) Inhibition of endothelial cell migration. HUVEC cells were allowed to migrate for 6 h toward serum (5% FBS) in the absence (control) or in the presence of indicated concentrations of human parstatin. Representative photomicrographs are shown. (F) HUVEC cells were allowed to migrate for 6 hours towards serum in the absence (control) or presence of human parstatin (parst), mouse parstatin (m-parst, 10 μM), short parstatin (shrt-parst, 10 μM), or scrambled parstatin (scr-parst, 10 μM). Migrated cells were fixed, stained and counted in six high-magnification microscopic fields (HMMF). Data are expressed as mean±SE; *$P<0.05$, **$P<0.01$
Figure 3:
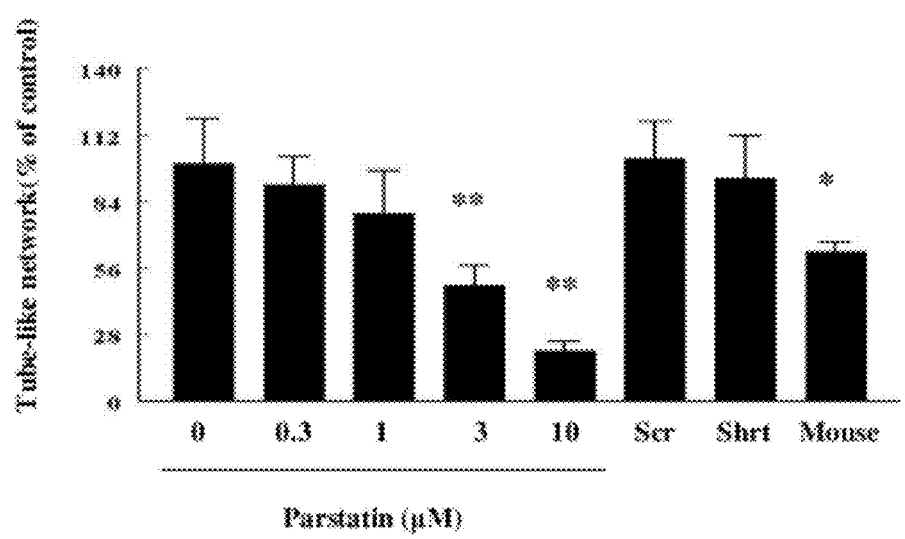
Figure 3:
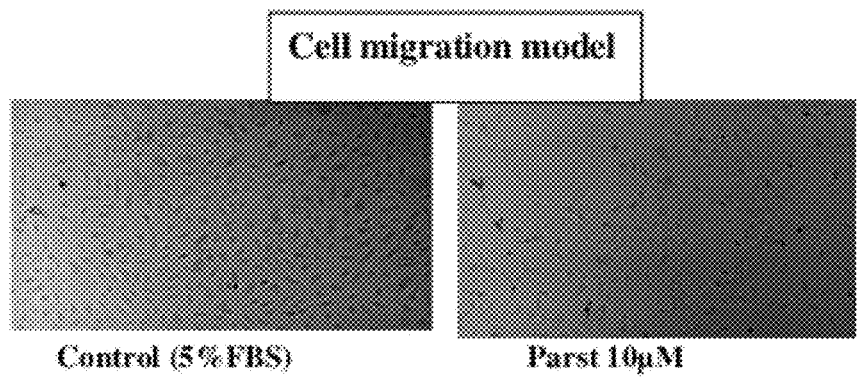
Figure 3:
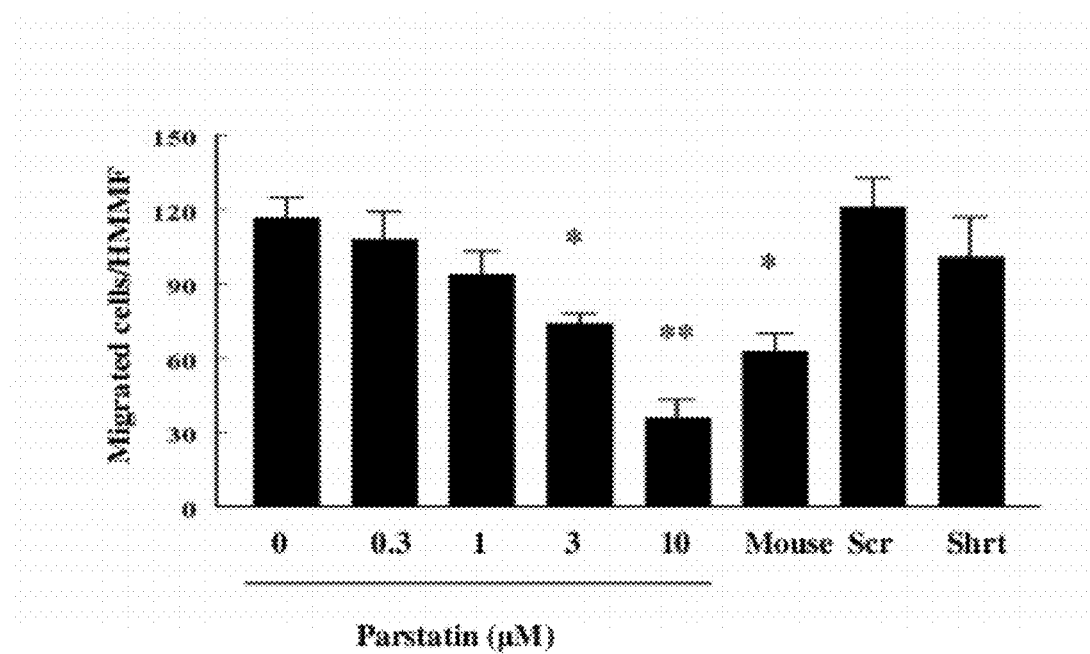

Cells were treated with increasing concentrations of human parstatin, scrambled parstatin, or short parstatin. After 18 hours of incubation, the medium was removed, and the cells were fixed and stained, and tube-like structures were quantitated. Results are shown in FIG. 3.

When parstatin was tested in Matrigel™ model, it exhibited a significant inhibitory effect on the rate and extent of tube formation (FIGS. 3A and B). At concentrations ranging from 0.3 to 10 µM, parstatin caused a dose-dependent inhibition of tube formation by endothelial cells plated on medium containing 5% serum. Mouse parstatin was effective in inhibiting tube formation by human cells (FIG. 3B).

The ability of endothelial cells to form three-dimensional structures was analyzed using a Fibrin gel in vitro angiogenesis assay kit (Chemicon International Inc. Temecula, Calif.). Fibrin gels were formed in 48-well plates by mixing fibrinogen and thrombin solutions, according to manufacturer instructions. Cells (40,000 cells/well) were then added and cultured in medium containing 2% FBS for 18 h. After the addition of a second layer of fibrin gel, endothelial cells sandwiched within fibrin gels were cultured in serum-free medium containing 0.5% bovine serum albumin (BSA) and the combination of VEGF/bFGF for 24 h. Where indicated, parstatin or other peptides were added. Capillary-like network was photographed and measured.

Similar results were evident in fibrin in vitro angiogenesis model as in the tube formation model, where endothelial cells were cultured in a sandwich mode between two fibrin gels, and formed capillary-like tubes in 3 dimensions (FIGS. 3C and D). The total capillary tube length induced by VEGF and bFGF was significantly reduced by parstatin. Control scrambled parstatin and short parstatin did not affect the ability of endothelial cells to form capillary-like networks in either model (FIGS. 3B and D). Exposure of endothelial cells to mouse parstatin resulted in a less pronounced, but still significant, inhibitory effect. These data further demonstrate the effectiveness of parstatin peptides as anti-angiogenic agents both within and across species.

Example 5

Parstatin Inhibits Cell Migration of Endothelial Cells

HUVEC cell migration was assessed using a modified Boyden's chamber assay, i.e., in Transwell cell culture chambers (Corning Life Sciences, Acton, Mass.). Briefly, polycarbonate filters with 8 µm pores were used to separate the upper and the lower chambers. Cells were added to the upper compartment at a density of 10,000 cells/100 µl in serum-free medium containing 0.5% BSA and incubated for 6 h. Directional migration (chemotaxis) in the lower chamber was induced by addition of medium containing 5% FBS to the lower chamber. Where indicated parstatin or other peptides were added to lower chamber.

Cells on the filters were fixed and stained. The non-migrated cells (cells in upper surface) were removed by wiping with cotton swabs. The cells on the lower surface were counted manually under microscope in six predetermined fields. Parstatin attenuated chemotactic cell migration through microporous membrane in response to serum (FIGS. 3E and F). When human parstatin was combined with 5% FBS, the number of migrated cells was reduced in concentration-dependent manner. Again, scrambled parstatin and short parstatins were without effect. Mouse parstatin caused a significant inhibitory effect, but to a lower extent as compared to human parstatin. These data demonstrate that parstatin can have an anti-angiogenic effect by decreasing cell migration, a required step in angiogenesis.

Example 6

Parstatin Inhibits Growth of Endothelial Cells

Cell proliferation was evaluated using a 3-(4,5-dimethyl-2-yl)-2,5-diphenyltetrazolium bromide (MTT, Sigma-Aldrich, St.Louis, Mo.) assay. Endothelial cells (10,000/well) were seeded in 24-well tissue culture plates and incubated with growth medium for 24 h. Cells were then treated with the vehicle or the indicated peptides in medium containing 5% FBS for 1 to 3 days. After 24, 48, or 72 hours, MTT solution (5 mg/ml) was added to each well and incubated for 3 h at 37° C. The blue formazan crystals were solubilized by addition of DMSO and absorbance at 450 nm was recorded using a 96-well plate reader.

Figure 4:
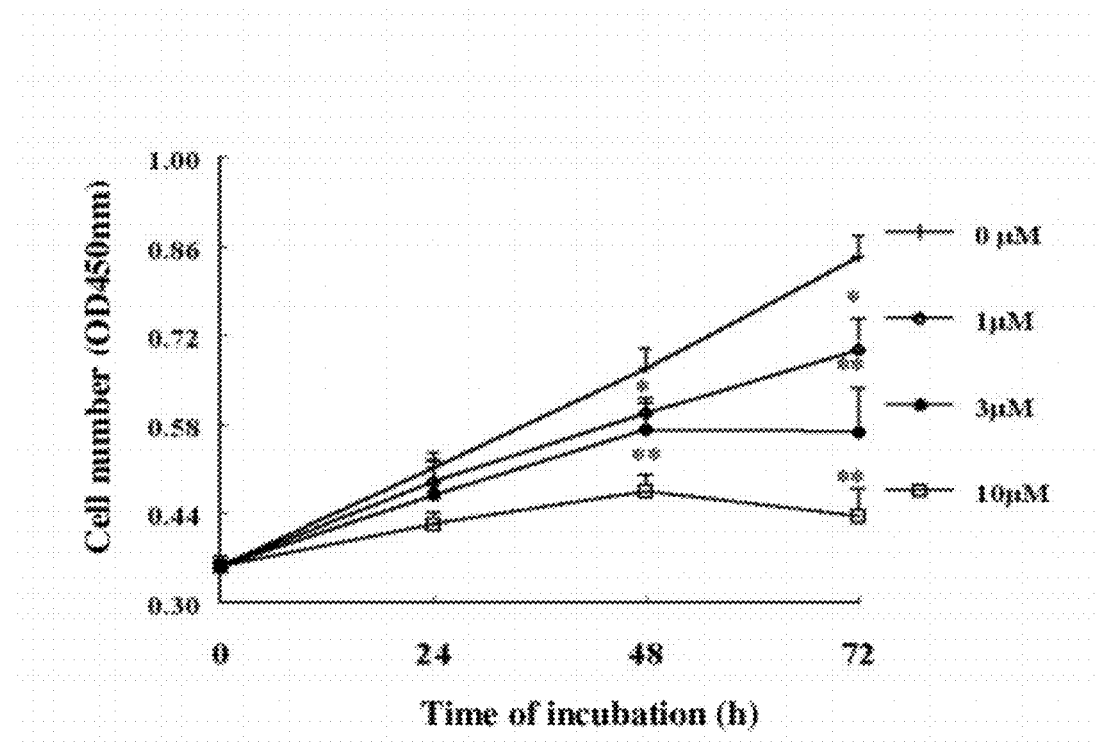
FIG. 4: Inhibition of endothelial cell proliferation by parstatin. (A) HUVEC cells were incubated in medium containing 5% FBS with increasing concentration of human parstatin as indicated and observed at 24, 48, and 72 hours for proliferation. (B) HUVEC cells were grown in the presence of 10 mM human parstatin, 10 μM mouse parstatin, or scrambled parstatin (scr-parst), or short parstatin (shrt-parst). Estimation of cell growth (proliferation) was performed 48 h after the beginning of treatments with parstatin. Results are expressed as mean±S.E. of absorption at 450 nm. *$P<0.05$, $P<0.01$
Figure 4:
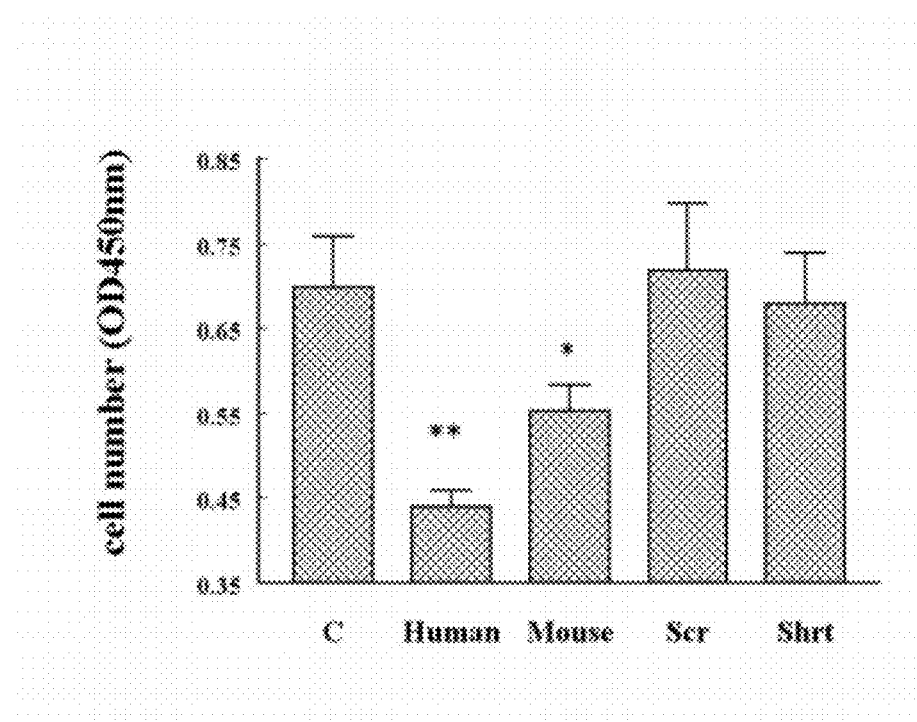

As shown in FIG. 4A, endothelial cell number doubled every 18 to 26 h over the 72-h period. In the presence of parstatin, the rate of endothelial cell growth was significantly decreased. HUVEC cell proliferation was essentially blocked by parstatin at 10 µM. This inhibitory effect of parstatin was dose-dependent with half-maximal inhibitory concentration at approximately 3 µM.

Similar results were also obtained when cell growth was stimulated by VEGF or bFGF with half-maximal inhibitory concentration of 1 µM for parstatin. Mouse parstatin was less effective inhibiting cell proliferation with half-maximal concentration at 20 µM, whereas scrambled parstatin and short parstatin were without effect (FIG. 4B). These data demonstrate that parstatin decreases the rate of endothelial cell proliferation both within and across species.

Example 7

Parstatin Inhibits DNA Synthesis in Endothelial Cells

The ability of parstatin to inhibit DNA synthesis of endothelial cells was assessed in thymidine incorporation assays. HUVEC cells were grown until 60-80% confluent in 24-well plates. Cells were treated with indicated peptides in serum-free medium containing 0.5% BSA, VEGF, bFGF, medium containing 5% FBS, epidermal growth factor (EGF), or heparin-binging EGF (HB-EGF) for 18 hours. All cells were pulsed with 0.5 µCi/ml [$^3$H]-thymidine (ICN Biomedicals Inc., Irvine Calif.) for additional 6 h. Radioactivity incorporated into DNA was determined in liquid scintillation counter.

Figure 5:
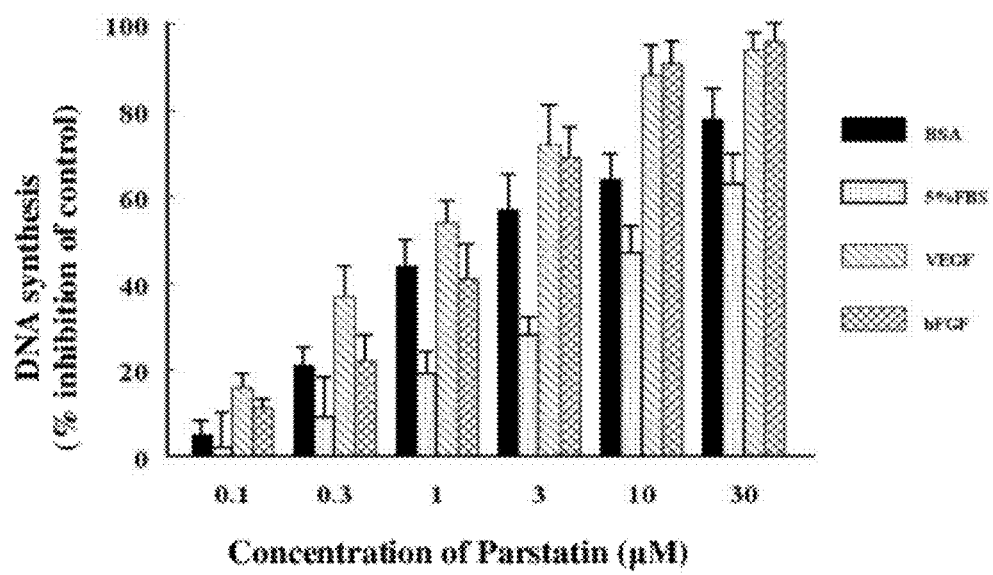
FIG. 5: Inhibition of endothelial cell DNA synthesis by parstatin. (A) HUVEC cells were incubated in medium containing either 0.5% bovine serum albumin (BSA), 5% fetal bovine serum (FBS), VEGF (10 ng/ml), or bFGF (5 ng/ml) in the presence of increasing concentrations of human parstatin for 18 hours. DNA synthesis was quantitated as a percent of inhibition relative to a control (non-parstatin treated) sample. (B) HUVEC cells were incubated in medium containing either 0.5% bovine serum albumin (BSA) or bFGF (5 ng/ml) or EGF (10 ng/ml) or HB-EGF (50 ng/ml) in the presence of human parstatin (parst, 10 μM) for 18 hours. All cells were pulsed with [$^3$H]thymidine for an additional 6 hours. DNA synthesis was quantitated as a percent of inhibition relative to a control (non-parstatin treated) sample. Results are expressed as mean±S.E. of dpm per well and presented as percentage inhibition of control. $P<0.01$
Figure 5:
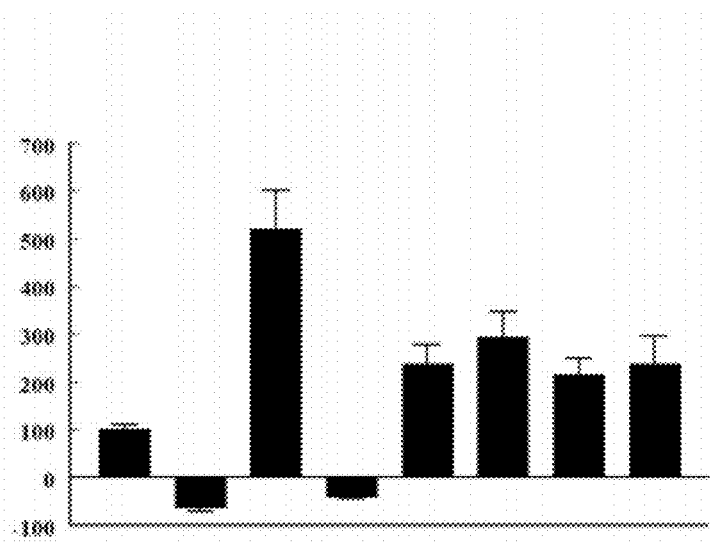

As shown in FIG. 5A, parstatin reduced DNA synthesis in HUVEC cells in a dose-dependent manner, with the inhibitory effect on bFGF- or VEGF-stimulated DNA synthesis to be more substantial than that of serum. These data demonstrate more potent activity of parstatin on dividing cells rather than quiescent cells.

When DNA synthesis experiments were repeated with cells that were in quiescent state (100% confluent), the inhibitory effect of parstatin was less pronounced (21.6%±7.4 inhibition by 10 µM parstatin in 5% FBS versus 47.3±6.1 on fast-growing cells), indicating a more substantial inhibitory effect for parstatin on stimulated endothelial cells.

The continuous presence of parstatin in cell culture was not necessary, since DNA synthesis inhibition was also evident after short exposure of cells to parstatin. Even at the earlier time studied of 30 min exposure, the inhibition of VEGF-induced DNA synthesis was 70% of the maximum (exposure for 24 h) and did not increase further after 1 h exposure to parstatin. These data demonstrate that a single dose of parstatin can have a sustained effect.

As in cell proliferation experiments, mouse parstatin exhibited a significant, but less effective inhibitory effect. Scrambled parstatin and short parstatin did not cause any significant effect demonstrating specificity of the parstatin peptides as anti-angiogenic agents.

Example 8

Parstatin Inhibits Signaling Through the MAP Kinase Pathway

The MAPK (Erk1/2, p42/44) cascade mediates mitogenesis. Cell cycle progression has been shown to depend on sustained activation of the Erk signal transduction pathway. HUVEC cells were cultured in 35 mm tissue culture dishes. After reaching 80% confluency, cells were growth factor-starved and subsequently stimulated for 10 min with vehicle or indicated agents. In combination experiments, cells were pretreated with parstatin or other peptides for 10 to 60 min.

Attached cells were lysed with Laenmli sample buffer, resolved in 10% SDS-PAGE, and transferred to nitrocellulose membranes. Membranes were incubated with primary antibodies against phospho p42/44 mitogen-activated protein kinases (p-Erk1/2, New England Biolabs, UK) and p42/44 Erk1/2 (t-Erk1/2, New England Biolabs, UK). Membranes were then probed with secondary antibodies horseradish peroxidase-conjugated, and proteins were visualized by chemiluminescent detection.

Figure 6:
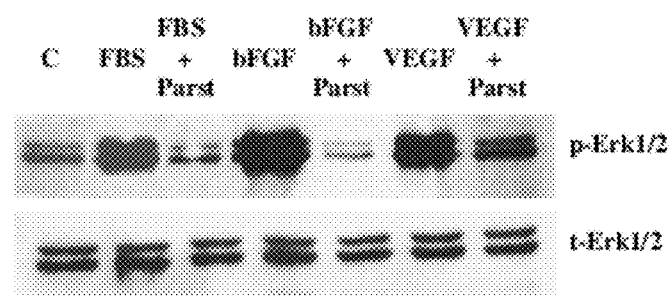
FIG. 6: Inhibition of MAPK activation in endothelial cells by parstatin. (A) Serum-starved HUVEC cells were pretreated with human parstatin (10 μM) for 1 h and then stimulated with 5% serum (FBS), bFGF (5 ng/ml), or VEGF (10 ng/ml) for 10 min. Western blots were performed using antibodies against phosphorylated ERK-1/2 (p-ERK1/2) or total ERK-1/2 (tERK-1/2). "C" over the leftmost lane of the blot indicates control lysate from unstimulated cells. (B) HUVEC cells were pretreated with indicated concentrations of parstatin for 1 h and then stimulated with bFGF (5 ng/ml) for 10 min. Western blots were performed using antibodies against phosphorylated ERK-1/2 (p-ERK1/2) or total ERK-1/2 (tERK-1/2). "C" over the leftmost lane of the blot indicates control lysate from unstimulated cells. (C) HUVEC cells were pretreated with human parstatin (10 µM) for indicated time periods, or with scramble parstatin (Scr) or mouse parstatin (Mouse) for 1 h and then stimulated with bFGF (5 ng/ml) for 10 min. Western blots were performed using antibodies against phosphorylated ERK-1/2 (p-ERK1/2) or total ERK-1/2 (tERK-1/2). "C" over the leftmost lane of the blot indicates control lysate from unstimulated cells. (D) HUVEC cells were pretreated with human parstatin (10 µM) for 1 h and then stimulated with bFGF (5 ng/ml) or washed (removal of parstatin) and incubated in fresh medium for addition indicated time periods and then stimulated with bFGF (5 ng/ml). Western blots were performed using antibodies against phosphorylated ERK-1/2 (p-ERK1/2) or total ERK-1/2 (tERK-1/2). (E) Serum-starved HUVEC cells were pretreated with human parstatin (parst, 10 µM) for 1 h and then stimulated with bFGF (5 ng/ml), EGF (10 ng/ml), or HB-EGF (50 ng/ml) for 10 min. Total cell lysates were probed with antiphospho Erk1/2-specific antibody (p-ERK1/2). To determine total protein level, membranes were probed with Erk1/2 antibody (t-ERK1/2). Representative membrane blots are shown for all A-E.
Figure 6:
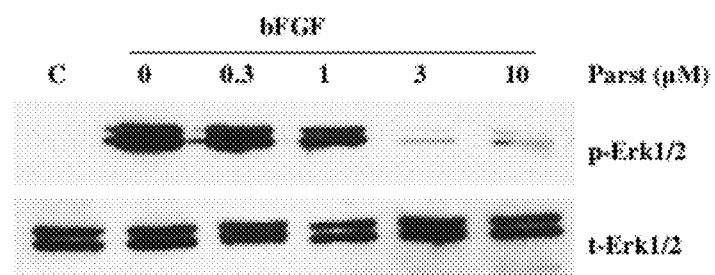
Figure 6:
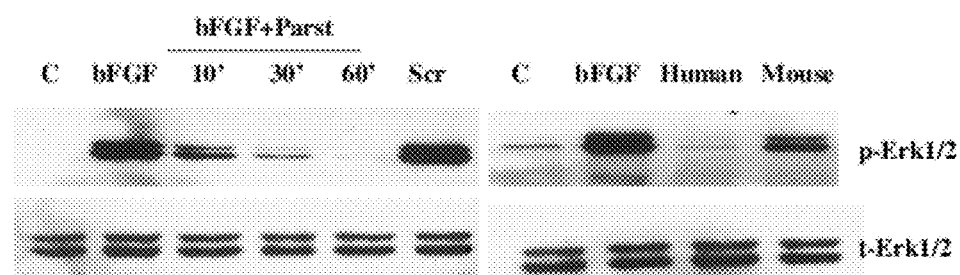
Figure 6:
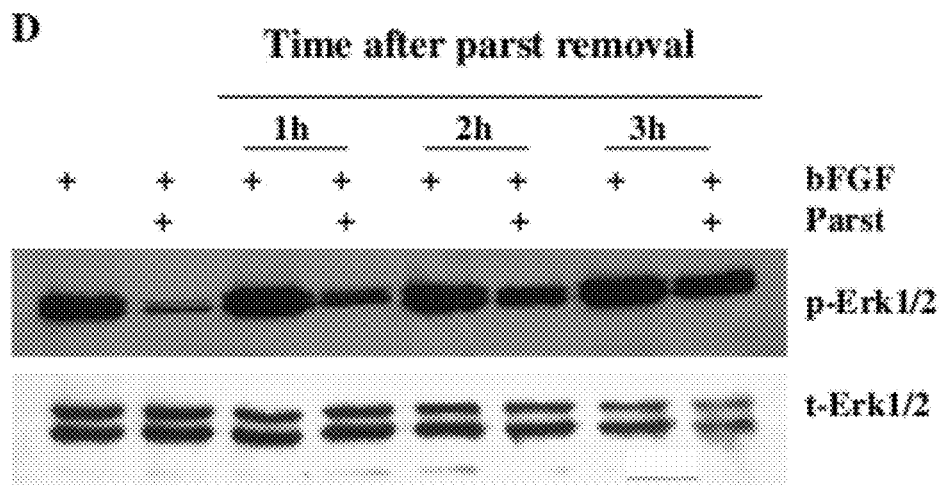
Figure 6:
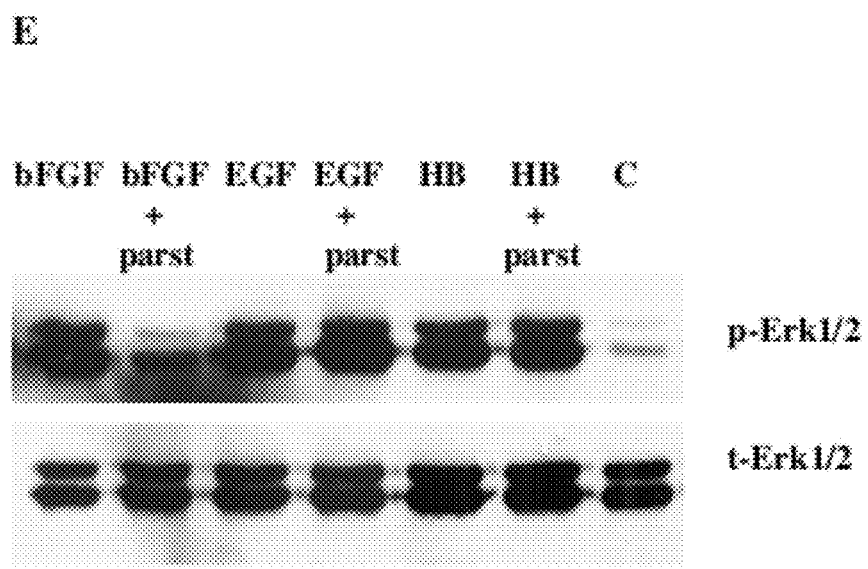

As shown in FIG. 6A, pretreatment of endothelial cells with parstatin for 1 h inhibited the activation of Erk1/2 stimulated either by FBS, bFGF, or VEGF. The inhibitory effect was concentration-dependent. Parstatin essentially blocked the bFGF-induced Erk1/2 phosphorylation levels from a concentration of 3 μM (FIG. 6B). This inhibitory effect was observed at the shortest exposure times. For example, at 10 min, the inhibition of Erk1/2 activation was about 50% of the maximum, indicating a time-dependent effect of parstatin (FIG. 6C).

The blockage of Erk1/2 phosphorylation by parstatin was found to be almost completely reversible (FIG. 6D). HUVEC cells exposed to human parstatin for 1 h, then washed free of parstatin, and subsequently incubated for further 1 to 3 hours in fresh medium, regained the ability to respond in bFGF and to stimulate the phosphorylation of Erk1/2. As expected scrambled parstatin did not alter the Erk1/2 activation and mouse parstatin had a less pronounced effect as compared to human parstatin at similar concentrations (FIG. 6C).

Interestingly, the growth inhibitory effect of parstatin was specific for bFGF or VEGF, since parstatin did not have any effect on EGF- or HB-EGF-induced DNA synthesis (FIG. 5B) and Erk1/2 activation (FIG. 6E). These results may provide insight to the mechanism of action of parstatin in the inhibition of cell proliferation and migration.

Example 9

Parstatin Inhibits Growth of Endothelial Cells is Associated and Induction of Apoptosis as Demonstrated by Flow Cytometery Flow-cytometric cell cycle analysis was performed to determine whether the inhibitory effect of parstatin on cell growth was a reflection of cytostatic or cytotoxic effects due to cell cycle arrest and apoptosis. HUVEC cells grown in 100 mm tissue culture plates to approximately 80% confluence, were treated in absence or in presence of parstatin for 24 h in serum-free medium containing either 0.5% BSA or bFGF.

Attached cells were collected by trypsinization, pooled with suspended cells, washed, and fixed. Fixed cells were then stained with propidium iodide (50 μg/ml, Sigma-Aldrich, St. Louis, Mo.) for 20 min at 4° C. in the dark. Flow cytometry was performed on a FACS flow cytometer (EPICS XL-MCL; Coulter). The propidium iodide-stained cell population in sub-Go/G1, G1, S, and G2/M phases were represented by distinct and quantified peaks in the fluorescence histograms obtained using the WinMDI logiciel program.

Figure 7:
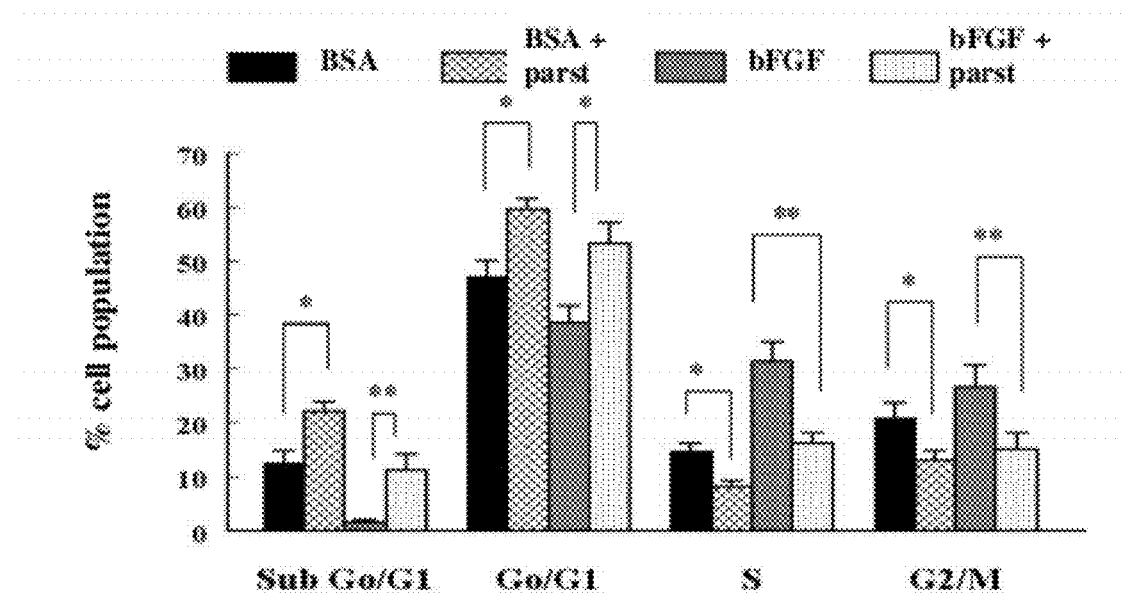
FIG. 7: Effect of parstatin on endothelial cell cycle progression. Subconfluent HUVEC cells were incubated in medium containing either 0.5% bovine serum albumin (BSA) or bFGF (5 ng/ml) in the presence of vehicle or human parstatin (10 µM) for 24 hours. Cells were harvested with trypsin, stained with propidium iodide and analyzed with a flow cytometer. The mean±SE of percentage of cells in sub-Go/G1, G1, S, and G2/M phases of the cell cycle are shown, as determined from the histogram of propidium iodide-stained cells. *$P<0.05$, **$P<0.01$.

As shown in FIG. 7, human parstatin increased the subGo/G1 cell fraction (subdiploid region on the DNA content histogram), which represents the percentage of apoptotic cells. In addition, parstatin increased the cell fraction in Go/G1 phase, indicating that it induced endothelial cell cycle arrest. In agreement with results obtained in growth experiments, parstatin reduced the percentages of cells in S and G2/M phases. Similar results were obtained when endothelial cells stimulated by growth factors, such as bFGF (FIG. 7). These data demonstrate an inhibition of cell cycle progression by various angiogenic agonists.

Example 10

Parstatin Inhibits Growth of Endothelial Cells is Associated and Induction of Apoptosis as Demonstrated by Cell Staining The role of parstatin in endothelial cell apoptosis was further explored using the Annexin V/propidium iodide based assay (Annexin V-FITC assay kit, BD Biosciences PharMingen, Belgium), which is a valuable and very sensitive technique to detect apoptosis. Endothelial cells were grown until approximately 80% confluence. Cells were then treated in the absence or in the presence of human parstatin for 24 h in serum-free medium containing either 0.5% BSA, VEGF, or bFGF. The broad spectrum caspase inhibitor Z-VAD-FMK (Z-Val-Ala-Asp(OCH$_3$)-Fluoromethylketone) was used alone or in combination with parstatin at a fixed 100 μM concentration. Attached cells were pooled with suspended cells and resuspended in 100 μL of the kit reaction buffer containing propidium iodide and Annexin V-FITC, according to the manufacturer's instructions. Cells were analyzed on FACS flow cytometer within 1 h after staining. Cells were analyzed for healthy cells (annexin V- and PI-negative), early apoptotic cells (annexin V-positive, PI-negative) and late apoptotic or dead cells (annexin V- and PI-positive).

Figure 8:
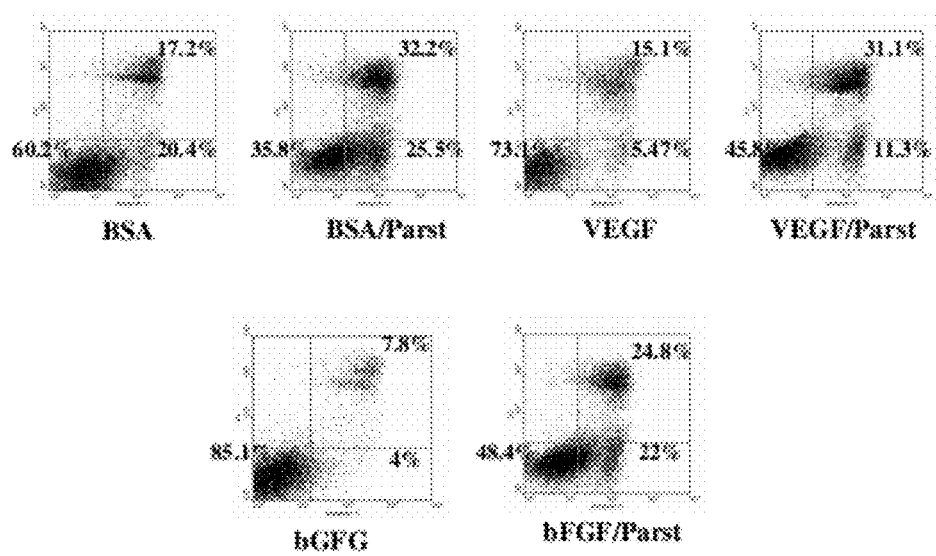
FIG. 8: Effect of parstatin on annexin V/propidium iodide (PI) double staining for apoptosis in endothelial cells. (A) Subconfluent HUVEC cells were incubated in medium containing either 0.5% bovine serum albumin (BSA), VEGF (10 ng/ml), or bFGF (5 ng/ml) in the presence of vehicle or human parstatin (10 µM) for 24 hours. The corresponding percentages of stained cells are shown in representative scatter plots. (B) HUVEC cells were incubated in medium containing 0.5% bovine serum albumin (BSA) in the presence of vehicle or indicated concentrations of human parstatin, caspase inhibitor Z-VAD-FMK (100 µM), or the indicated combination for 24 hours. Cells were fixed, stained with annexin V-FITC and PI and analyzed for healthy cells (annexin V- and PI-negative, bottom left), early apoptotic cells (annexin V-positive and PI-negative, bottom right) and late apoptotic or dead cells (annexin V- and PI-positive, top right) by flow cytometry. Results are expressed as mean percentage of cell population±SE. Statistical analysis was performed in early apoptotic cell population. *$P<0.05$, **$P<0.01$.
Figure 8:
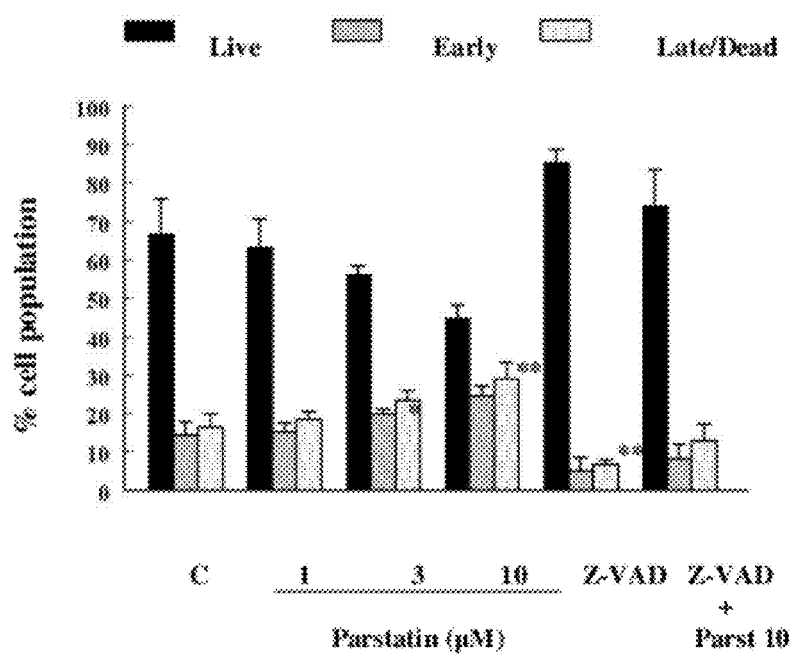

The data presented in FIG. 8A, revealed that parstatin increased the percentages of endothelial cells in early and late apoptotic stages. In parallel, the percentage of healthy/viable cells was equally decreased. Parstatin promoted cell apoptosis in all culture conditions used with the effect to be more pronounced in endothelial cells stimulated by bFGF or VEGF. The apoptotic effect of parstatin was concentration-dependent and was reversed by caspase inhibitor Z-VAD-FMK (FIG. 8B), indicating that caspase activation was involved in parstatin-mediated the apoptotic cell death.

Example 11

Parstatin Inhibits Growth of Endothelial Cells is Associated and Induction of Apoptosis as Demonstrated by Caspase Activation To further support the involvement of caspases in parstatin pro-apoptotic effect, its effect on caspase-3 activation was examined using a commercially available kit (Promega, Madison, Wis.). The colorimetric substrate, Ac-DEVD-p-nitroanilide, is cleaved by caspase-3 to release yellow p-nitroanilide, was measured by absorbance at 405 nm to detect caspase activation.

HUVEC cells were grown in 60 mm tissue culture plates until approximately 80% confluency. Cells were treated in absence or in presence of the indicated peptides for 24 h in serum-free medium containing either 0.5% BSA or bFGF. Suspended and adherent cells were collected and lysed. Caspase-3 activity was measured by absorbance at 405 nm.

Figure 9:
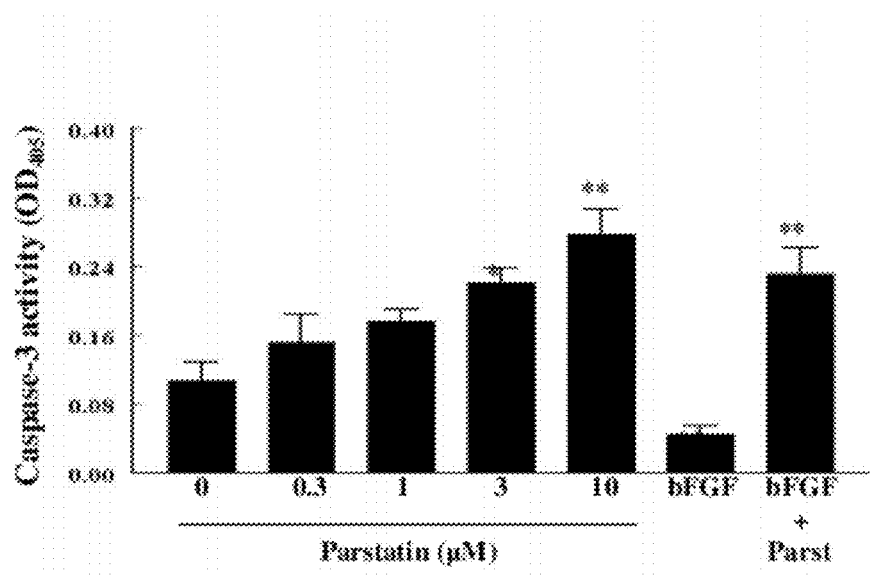
FIG. 9: Effect of parstatin on caspase-3 activity and poly (ADP-ribose) polymerase (PARP) cleavage. (A) Caspase-3 activity was determined in cell extracts of HUVEC cells cultured in medium containing either 0.5% bovine serum albumin or bFGF (5 ng/ml) in the presence of vehicle or indicated concentrations of human parstatin for 24 hours. Results are expressed as mean±SE of optical density at 405 nm ($OD_{405}$). *$P<0.05$, **$P<0.01$. (B) Caspase-3 activity was determined in cell extracts of HUVEC cells cultured in medium containing 0.5% bovine serum albumin in the presence of vehicle, human parstatin (10 µM, parst 10), Z-VAD-FMK (100 µM), mouse parstatin (10 µM, Mouse), scrambled parstatin (10 µM, Scr), or the indicated combination for 24 hours. Results are expressed as mean±SE of optical density at 405 nm ($OD_{405}$). *$P<0.05$, **$P<0.01$. (C) HUVEC cells were cultured in medium containing either 0.5% bovine serum albumin (BSA) or bFGF (5 ng/ml) in the presence of vehicle or indicated concentrations of human parstatin for 24 hours. Whole cell lysates were resolved by SDS-PAGE and immunoblotted with anti-PARP monoclonal antibody. Protein loading was confirmed by probing the membranes with α-tubulin antibody. Representative membrane blot is shown.
Figure 9:
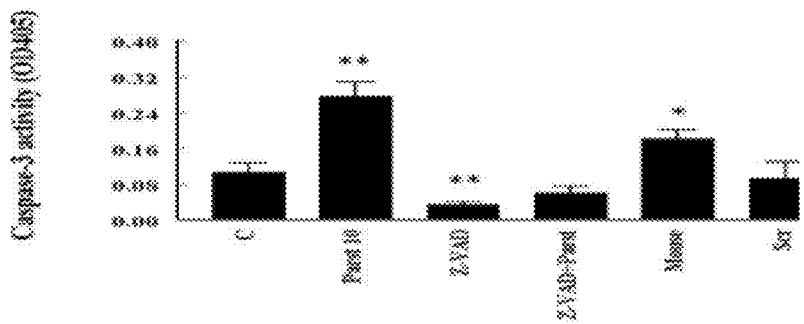
Figure 9:
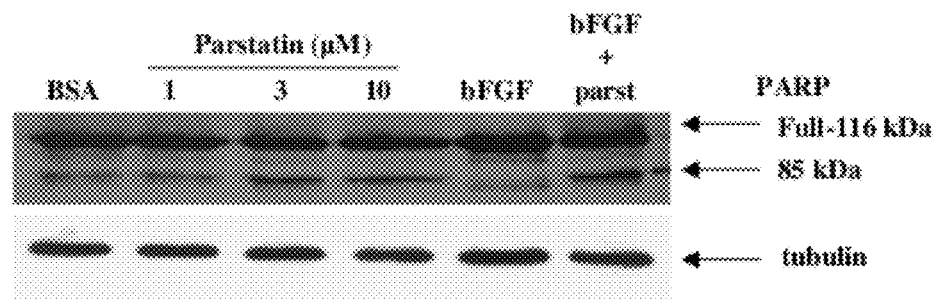

As shown in FIG. 9A, human parstatin increased the level of caspase-3 activity in concentration dependent manner. As expected, bFGF alone reduced significantly the activity of caspase-3, while when it was combined with parstatin the caspase-3 activity increased dramatically. The combination of parstatin with Z-VAD-FMK resulted in blockage of the action of parstatin, suggesting its specificity for caspase-3 (FIG. 9B). In addition, the promoting activity of parstatin was observed as early as 3 hours after the exposure of cell to parstatin. Mouse parstatin caused a moderate increase in caspase-3 activity and scrambled parstatin was without effect (FIG. 9B). These data again demonstrate cross-species, sequence specific activity of parstatins.

Example 12

Parstatin Inhibits Growth of Endothelial Cells is Associated and Induction of Apoptosis as Demonstrated by PARP Cleavage PARP is activated in response to DNA damage and is implicated in the repair of DNA strand breaks. PARP cleavage by caspases produces 85- and 24-kDa fragments from the full-length 116-kDa protein. This leads to its inactivation and constitute early events in apoptosis.

Western blotting for PARP cleavage was performed on cell lysates from HUVEC cells cultured in serum free medium containing BSA for 24 h. The presence of parstatin induced PARP cleavage to its signature 85-kDa fragment in concentration dependent manner (FIG. 9C). Parstatin also increased PARP cleavage in bFGF-stimulated endothelial cells. Together these results suggest that parstatin promoted apoptosis in growing endothelial cells and provide strong evidence that the cytotoxicity observed is due to caspase activation.

Example 13

Parstatin is a Cell-Penetrating Peptide

Some signal peptides due to their highly hydrophobic properties, possess the ability to interact with cell membrane lipid bilayers and to penetrate inside the cell (Lin et al, 1995, J Biol Chem, 270: 14255-14258). To investigate if parstatin exerts its cellular effects as a cell-permeable peptide, human parstatin and control peptides were conjugated with FITC. To measure the parstatin uptake into the endothelial cells, two methodological approaches were used: flow cytometry and fluorescence microscopy.

HUVEC cells in the exponential growth phase were exposed to various concentrations of parstatin-FITC in serum-free medium containing 0.5% BSA. After incubation times ranging from 1 min to 60 min, cells were washed extensively. Washed cells were incubated for 10 min with trypsin at 37° C. to remove the cell surface-bound parstatin. Suspended cells were subsequently centrifuged, washed, and analyzed on FACS flow cytometer (EPICS XL-MCL; Coulter).

Figure 10:
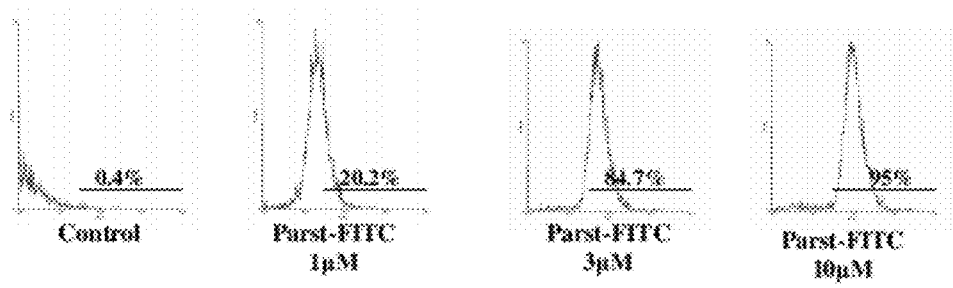
FIG. 10: Parstatin is a cell-penetrating peptide. (A) Histograms showing the effect of parstatin concentrations on cellular uptake. HUVEC cells were incubated with indicated concentrations of parstatin-FITC for 30 min. Trypsinized cells were analyzed by flow cytometry. The uptake of parstatin-FITC into cells was assessed by the change of the FITC-positive cell population compared with untreated control cell samples. (B) Histograms showing the cellular uptake of parstatin by the time. HUVEC cells were incubated with parstatin-FITC (10 µM) for the indicated time intervals. Trypsinized cells were analyzed by flow cytometry. The uptake of parstatin-FITC into cells was assessed by the change of the FITC-positive cell population compared with untreated control cell samples. (C) Fluorescence microscopy images. HUVEC cells were incubated with 10 µM parstatin-FITC (green) for the indicated time intervals and stained with the nuclear dye DAPI (blue). Arrows show the FITC signal localization on cell membrane or in cytosol.
Figure 10:
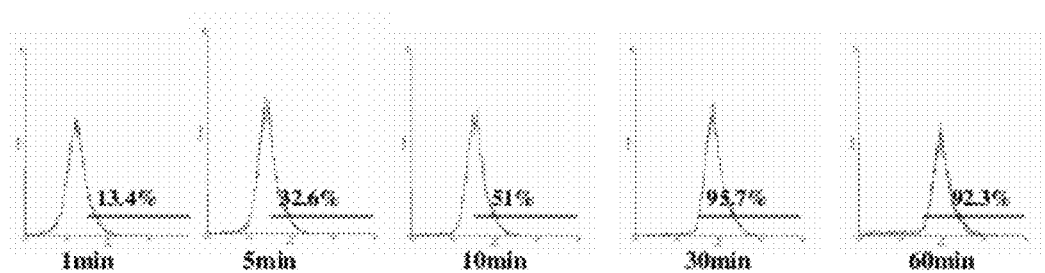
Figure 10:
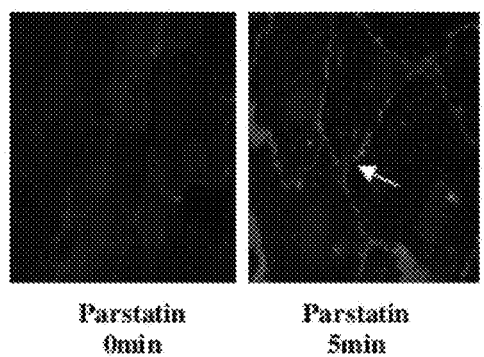

The uptake of a given parstatin-FITC into cells was assessed by the change of the FITC-positive cell population compared with untreated control cell samples. As shown in FIG. 10A, the fraction of FITC-positive cell population exposed to parstatin-FITC for 30 min was increased in a dose-dependent manner. In addition, the uptake kinetics of parstatin into endothelial cells suggested a non-saturable, non-receptor mediated uptake (FIG. 10B). Even at the shortest time of exposure to parstatin studied of 1 min the FITC-positive cell population was 13.4% and reached to maximal level after 30 min of treatment.

For imaging, endothelial cells were incubated with FITC-labelled parstatin as described above and the distribution of parstatin was observed with fluorescent microscopy. 4',6-Diamidino-2-phenylindole (DAPI) was used to stain nuclei of all cells. Cell fluorescence was imaged on a Nikon Eclipse TE2000-U microscope. FITC and DAPI were excited using 490-nm and 360-nm filters, respectively. The emission signals were sorted out using 514 and 460 filters for the FITC and DAPI, respectively.

FIG. 10C shows the images obtained for HUVEC cells treated with 10 µM of parstatin-FITC for different time intervals. In control sample, for which no fluorescence was observed, cells were not exposed to parstatin-FITC. FITC signal (green) was detected as early as 5 min of cell exposure to parstatin-FITC. At this time point, parstatin signal was exclusively localized in cell membranes. When endothelial cells were exposed to parstatin-FITC for 10 min the FITC signal was detected in cell membranes and in the cytosol. The exposure of cells for 30 min resulted in signal localization only in the cytosol, preferentially around the nucleus.

These data suggest that parstatin possess the ability to interact with cell membranes and enter cells at a rate dependent on the exposure time and the concentration applied. They also suggest that parstatin peptides may be exceptionally useful and readily taken up in topical or local applications (e.g., intraocular injections for the treatment of retinal angiogenesis). This kinetic profile was in agreement with the initiation of parstatin-mediated biological effects (e.g. the inhibition of bFGF-induced MAPK activation). These data also suggests that cell membrane fluidity and membrane protein mobility were important for parstatin cell penetration, because low temperature or pretreatment of cells with paraformaldehyde prevents parstatin peptide uptake. In addition receptor-mediated uptake does not seem to be involved. An excess of unlabeled peptide, the inhibitors of endosomal/lysosomal uptake, and an inhibitor of protein synthesis (cycloheximide) were without effect on peptide uptake. Taken together, these results provide evidence that parstatin is a cell-penetrating peptide which exerts its biological effects intracellularly.

Example 14

Parstatin Attenuates Myocardial Ischemia-Reperfusion Injury in Rats

Parstatin was used in an in vivo rat model of cardiac ischemia and reperfusion, and in an in vitro isolated rat heart model of ischemia-reperfusion injury. Male Sprague Dawley rats at 8 weeks of age were used and treated in compliance with the "Guide for the Care and Use of Laboratory Animals" formulated by the National Research Council (USA), 1996.

For in vivo infarct size studies, rats were anesthetized with pentobarbital sodium (50 mg/Kg) and heparin (1000 IU/Kg) and underwent 30 min of regional ischemia followed by 180 min of reperfusion. Parstatin was administered intravenously over 1 min starting 15 min prior to ischemia, 15 min after the onset of ischemia, and 5 min after the onset of reperfusion in a separate series of experiments (n=6/group).

To induce ischemia, ligature was positioned around the left main coronary artery and threaded through a plastic snare to permit reversible occlusion of the coronary artery. Coronary occlusion was induced by clamping the snare onto the heart and reperfusion was achieved by releasing the snare. At the end of reperfusion, the coronary artery was re-occluded and the risk zone was delineated by perfusion 0.5% Evans' blue into the aortic cannula.

Figure 11:
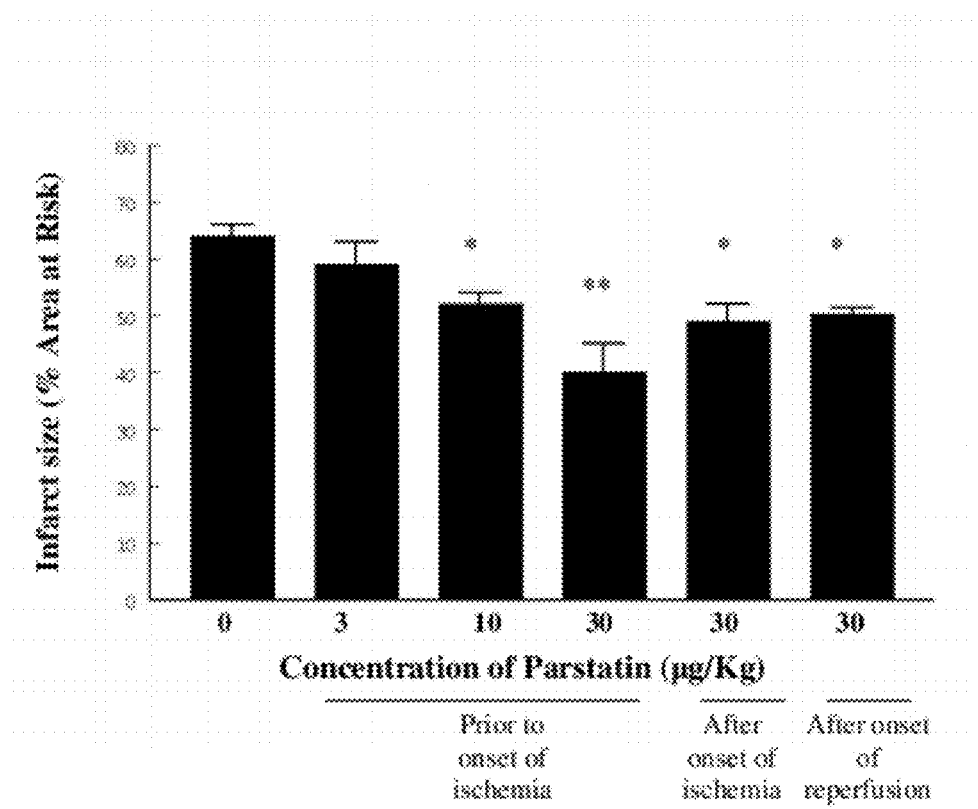
FIG. 11: Cardioprotective effect of parstatin in rat ischemia/reperfusion injury model in vivo. Rats were treated with either saline or increasing concentrations of human parstatin administered as an intravascular bolus 15 min prior to ischemia, 15 min after onset of ischemia, or 10 sec after onset or reperfusion. Results are expressed as mean±SE. n=6 rats/group. *$P<0.05$, **$P<0.01$.

Hearts were sectioned and incubated in 1% triphenyltetrazolium chloride in phosphate buffer for 15 min to define white necrotic tissue when fixed in 10% formalin for 24 h. Area at risk (AAR) and infarct-to-risk rations were determined by computerized planimetry using J-Image v.i.6 software (NIH, Bethesda, Mass.). As shown in FIG. 11, infarct size was 64±2% of the AAR in the control group. In rats that received parstatin, a concentration-dependant reduction in infarct size was seen, with an optimal dose at 30 µg/Kg. These hearts had an infarct size of 40±5, which is a 37.5% reduction in infarct size compared to the control.

Heart rate and blood pressures were monitored throughout the procedure and there were no significant differences between baseline hemodynamics of the groups. Mean arterial pressure decreased during ischemia and reperfusion in all groups but there was no significant difference between groups. In addition, rats were treated with an IV bolus of 30 µg/Kg of parstatin 15 min after the onset of ischemia or 5 minutes after initiation of reperfusion. Parstatin was able to reduce infarct size when administered during ischemia by 25% and at reperfusion by 21% when compared to control (FIG. 11). These data demonstrate that parstatin peptides are useful for both prophylaxis and treatment of ischemia/reperfusion injury.

Example 15

Parstatin Attenuates Myocardial Ischemia-Reperfusion Injury in Excised Hearts

For in vitro studies, excised hearts were retrograde perfused through the aorta with a modified Krebs buffer. Coronary flow rate was determined by timed collection of the coronary effluent. A saline-filled latex ballon connected to a pressure transducer was inserted into the left vertical (LV), and baseline end-diastolic pressure was set at 5-10 mmHg. Heart rate, LV end-diastolic pressure and LV developed pressures (LVDP) were recorded continuously. The measurements for post-ischemic recovery of LVDP used for comparison were taken at 180 min of reperfusion. After stabilization for 15-20 min, the hearts (n=6/group) were subjected to 30 min of regional ischemia, followed by 180 min of reperfusion.

Figure 12:
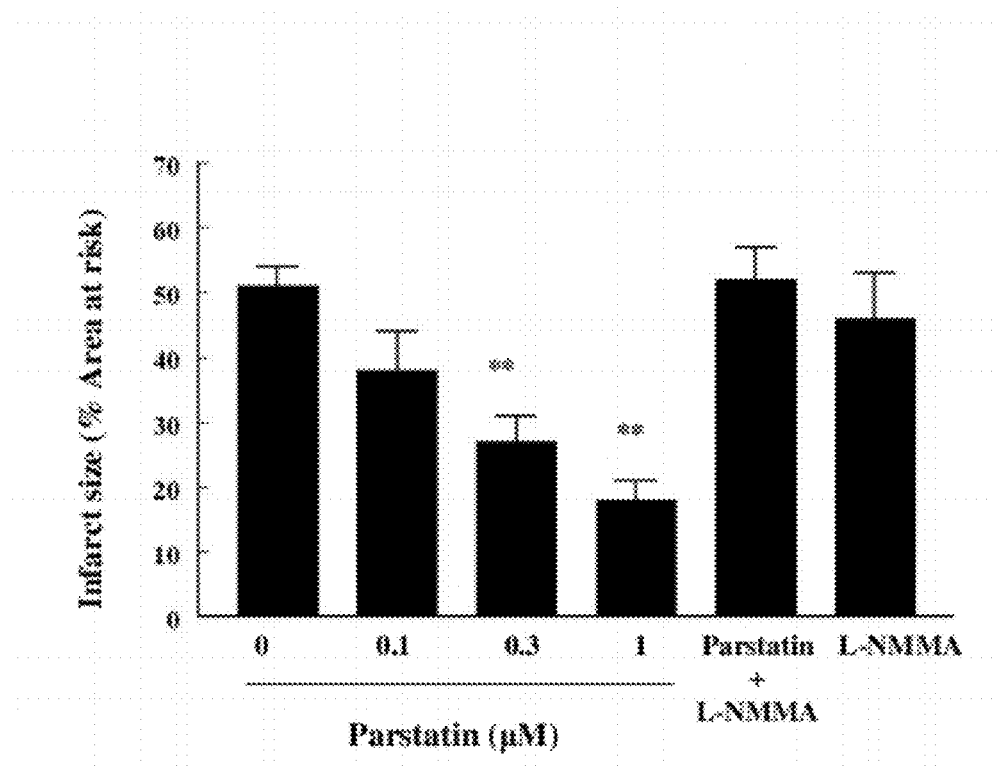
FIG. 12: Cardioprotective effect of parstatin in rat ischemia/reperfusion injury model in vitro. Isolated rat hearts were perfused with either buffer, increasing concentrations of parstatin, nitric oxide synthase inhibitor L-NMMA (100 µM), or the indicated combination for 15 min prior to regional ischemia and reperfusion. (A) Infarct size expressed as a percentage of area at risk. (B) Recovery of left ventricular developed pressure (LVDP). Results are expressed as mean±SE. n=6 rats/group. **$P<0.01$.
Figure 12:
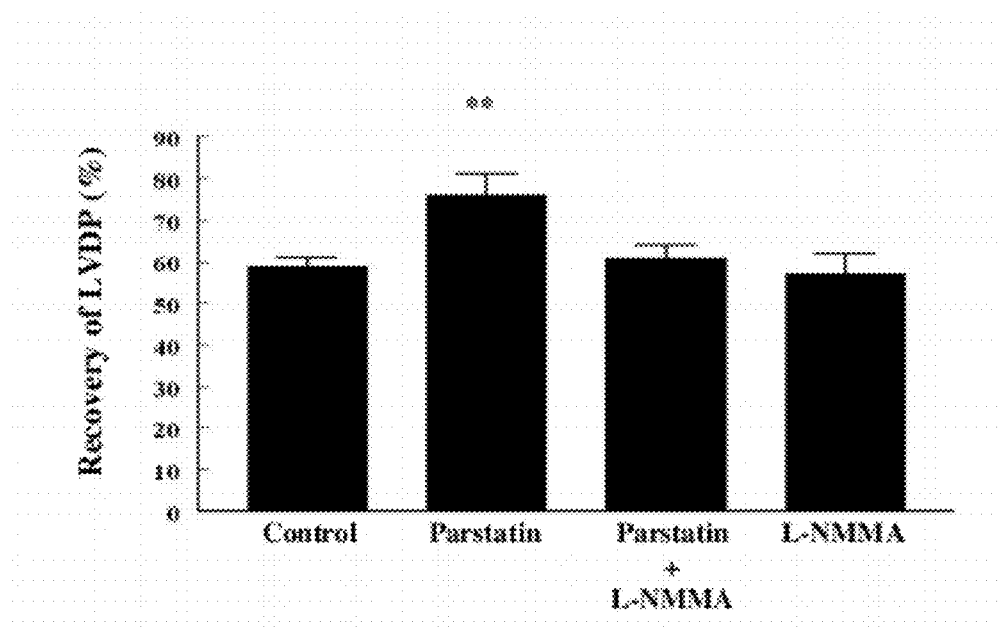

Different concentrations of parstatin were perfused 15 min prior to coronary occlusion until occlusion. L-NMMA, a specific inhibitor of nitric oxide synthase was perfused 15 min prior to addition of parstatin. As shown in FIG. 12A, controls hearts produced an infarct size of 51±3% of the AAR and continuous administration of parstatin resulted in a concentration-dependent reduction of infarct size. Parstatin at 1 μM led to the largest reduction in infarct size (18.3±3%), a 64% decrease. At this concentration, parstatin increased recovery of LVDP to a significant extent (76±5% versus 59±5% of control) (FIG. 12B). There were no differences in hemodynamics at any points measured between control and parstatin-treated groups. In addition, blockage of nitric oxide synthase by L-NMMA (100 μM) abolished the effect of parstatin, suggesting a role of nitric oxide pathway in cardioprotective action of parstatin (FIGS. 12A and B). Again, these data demonstrate the utility of parstatin peptides as both cardioprotective and therapeutic agents across species.

REFERENCES

1. Carmeliet P. Angiogenesis in life, disease and medicine. Nature, 2005; 438: 932-936.
2. Gariano R F, and Gardner T W. Retinal angiogenesis in development and disease. Nature, 2005; 438: 960-966.
3. Bainbridge J, et al. Angiogenesis as a therapeutic target in arthritis: lessons from oncology. Curr Pharm Des, 2006; 12: 2631-2644.
4. Yancopoulos G D, et al. Vascular-specific growth factors and blood vessel formation. Nature, 2000; 407: 242-248.
5. Nyberg P, et al. Endogenous inhibitors of angiogenesis. Cancer Res, 2005; 65: 3967-3979.
6. Khurana R, et al. Role of angiogenesis in cardiovascular disease. A critical appraisal. Circulation, 2005; 112: 1813-1824.
7. Moulton K S, et al. Angiogenesis inhibitors endostatin or TNP-470 reduce intimal neovascularization and plaque growth in apolipoprotein E-deficient mice. Circulation, 1999; 99: 1726-1732.
8. Moulton K S, et al. Inhibition of plaque neovascularization reduces macrophage accumulation and progression of advanced atherosclerosis. Proc Natl Acad Sci USA, 2003; 100: 4736-4741.
9. Di Cera E. Thrombin interactions. Chest, 2003; 124: 11S-17S
10. Tsopanoglou N E, and Maragoudakis, M E. Role of thrombin in angiogenesis and tumor progression. Semin Thromb Haemost, 2004; 30: 63-69.
11. Moser M, and Patterson C. Thrombin and vascular development. Arterioscler Thromb Vasc Biol, 2003; 23: 922-930.
12. Ossovskaya V S, et al. Protease-activated receptors: contribution to physiology and disease. Physiol Rev, 2004; 84: 579-621.
13. Vu T-K H, et al. Molecular cloning of a functional thrombin receptor reveals a novel proteolytic mechanism of receptor activation. Cell, 1991; 64: 1057-1068.
14. Leger A J, et al. Protease-activated receptors in cardiovascular diseases. Circulation, 2006; 114: 1070-1077.
15. Caunt M, et al. Thrombin induces neoangiogenesis in the chick chorioallontoic membrane. J Thromb Haemost, 2003; 1: 2097-2102.
16. Huang Y-Q, et al. Thrombin induces increased expression and secretion of VEGF from human FS4 fibroblasts, Du145 prostate cells and CHRF megakaryocytes. Thromb Haemost, 2001; 86: 1094-1098.
17. Huang Y-Q, et al. Thrombin induces increased expression and secretion of angiopoietin-2 from human umbilical vein endothelial cells. Blood, 2002; 99: 1646-1650.
18. Tsopanoglou N E, and Maragoudakis M E. On the mechanism of thrombin-induced angiogenesis: Potentiation of vascular endothelial growth factor activity on endothelial cells by up-regulation of its receptors. J Biol Chem, 1999; 274: 23969-23976.
19. Zucker S, et al. Thrombin induces the activation of progelatinase A in vascular endothelial cells. J Biol Chem, 1995; 270: 23730-23738.
20. Caunt M, et al. Growth-regulated oncogene is pivotal in thrombin-induced angiogenesis. Cancer Res, 2006; 66: 4125-4132.
21. Mohle R, et al. Constitute production and thrombin-induced release of VEGF by human megakaryocytes and platelets. Proc Natl Acad Sci USA 1997; 94: 663-668
22. Li J J, et al. Thrombin induces the release of angiopoietin-1 from platelets. Thromb Haemost, 2001; 85: 204-206.
23. Ma L, Proteinase-activated receptors 1 and 4 counter-regulate endostatin and VEGF release from human platelets. Proc Natl Acad Sci USA, 2005; 102: 216-220.
24. Olivot J-M, et al. Thrombomodulin prolongs thrombin-induced extracellular signal-regulated kinase phosphorylation and nuclear retention in endothelial cells. Circ Res, 2001; 88: 681-687.
25. Nierodzik M L, and Karpatkin, S. Thrombin induces tumor growth, metastasis, and angiogenesis: evidence for a thrombin-regulated dormant tumor phenotype. Cancer Cell, 2006; 10: 355-362.
26. Coughlin S R. Protease-activated receptors in hemostasis, thrombosis and vascular biology. J Thromb Hemost, 2005; 3: 1800-1814.
27. Nelken N A, et al. Thrombin receptor expression in normal and atherosclerotic human arteries. J Clin Invest, 1992; 90: 1614-1621.
28. Takada M, et al. Antibody to thrombin receptor inhibits neointimal smooth muscle cell accumulation without causing inhibition of platelet aggregation or altering hemostatic parameter after angioplasty in rats. Circ Res, 1998; 82: 980-987.

29. Cheung W M, et al. Altered vascular injury responses in mice deficient in protease-activated receptor-1. Arterioscler Thromb Vasc Biol, 1999; 19: 3014-3024.
30. Furman M I, et al. The cleaved peptide of the thrombin receptor is a strong platelet agonist. Proc Natl Acad Sci USA, 1998; 95: 3082-3087.
31. Furman M I, et al. The cleaved peptide of PAR1 results in a redistribution of the platelet surface GPIb-IX-V complex to the surface-connected canalicular system. Thromb Haemost, 2000; 84: 897-903.
32. Furman M I, et al. The cleaved peptide of PAR1 is a more potent stimulant of platelet-endothelial cell adhesion than is thrombin. J Vasc Surg, 2003; 37: 440-445.
33. Ferdinandy P, Schulz R, and Baxter G F. Interaction of cardiovascular risk factors with myocardial ischemia/reperfusion injury, preconditioning, and postconditioning. Pharmacol Rev, 2007; 59: 418-458.
34. Strande, J L, Hsu A, Su J, Fu X, Gross G J, and Baker J E. SCH 79797, a selective PAR1 antagonist, limits myocardial ischemia/reperfusion injury in rat hearts. Basic Res Cardiol, 2007; 102: 350-358.
35. Jameson B A, McDonnell J M, Marini J K, and Korngold R. A rationally designed CD4 analogue inhibits experimental allergic encephalomyelitis. Nature, 1994; 368: 744-746.
36. Brady L, and Dodson G. Drug design. Reflections on a peptide. Nature, 1994; 368: 692-693.

The invention claimed is:

1. A method of inhibiting endothelial cell growth in a mammal comprising:
    selecting the mammal as having an angiogenesis-related disease selected from the group consisting of diabetic retinopathy, retinopathy of prematurity, neovascular glaucoma, macular degeneration, chronic inflammation, arthritis, rheumatoid arthritis, osteoarthritis, ulcerative colitis, Crohn's disease, psoriasis, cancer, atherosclerosis, intimal hyperplasia, and pulmonary hypertension; and
    administering to the mammal a composition comprising a parstatin peptide consisting of SEQ ID NO: 1, thereby inhibiting endothelial cell growth in the mammal.

2. The method of claim 1, wherein inhibition of endothelial cell growth comprises at least one of inhibition endothelial cell proliferation, inhibition of DNA synthesis, and inhibition of mitogenic intracellular biochemical pathways as compared to endothelial cells not treated with SEQ ID NO: 1.

3. The method of claim 1, wherein inhibition of endothelial cell growth comprises inhibition of angiogenesis.

4. The method of claim 3, wherein inhibition of angiogenesis comprises inhibition of at least one of endothelial cell growth, endothelial cell migration, endothelial cell differentiation, and endothelial cell vascular-like tube formation as compared to endothelial cells not treated with SEQ ID NO: 1.

5. A method of inhibiting angiogenesis in a mammal comprising:
    selecting the mammal as having an angiogenesis-related disease selected from the group consisting of: diabetic retinopathy, retinopathy of prematurity, neovascular glaucoma, macular degeneration, chronic inflammation, arthritis, rheumatoid arthritis, osteoarthritis, ulcerative colitis, Crohn's disease, psoriasis, cancer, atherosclerosis, intimal hyperplasia, and pulmonary hypertension; and
    administering to the mammal a composition comprising a parstatin peptide consisting of SEQ ID NO: 1, thereby inhibiting angiogenesis.

6. The method of claim 1, wherein inhibition of cell growth comprises induction of apoptosis or cell cycle arrest as compared to endothelial cells not treated with SEQ ID NO: 1.

7. The method of claim 1, further comprising monitoring the mammal for inhibition of endothelial cell growth.

8. A method of treating an ischemia/reperfusion injury in mammalian myocardium comprising:
    selecting a mammal for treatment of the ischemia/reperfusion injury; and
    administering to the mammal a composition comprising a parstatin peptide consisting of SEQ ID NO: 1, thereby treating the ischemia/reperfusion injury in the mammal.

9. The method of claim 8, further comprising monitoring the mammal for prevention, amelioration, or treatment of ischemia/reperfusion injury.

10. A method for inhibiting angiogenesis in a mammal comprising:
    selecting the mammal as having an angiogenic sprout; and
    administering to the angiogenic sprout of the mammal in need thereof a composition comprising a parstatin peptide consisting of SEQ ID NO: 1, thereby inhibiting angiogenesis in the mammal.

11. The method of claim 1, wherein the mammal is a human.

12. The method of claim 8, wherein the mammal is a human.

13. The method of claim 10, wherein the mammal is a human.

14. The method of claim 5, wherein the mammal is a human.

* * * * *

```
                       SEQUENCE LISTING

<160> NUMBER OF SEQ ID NOS: 10

<210> SEQ ID NO 1
<211> LENGTH: 41
<212> TYPE: PRT
<213> ORGANISM: Homo sapiens

<400> SEQUENCE: 1

Met Gly Pro Arg Arg Leu Leu Leu Val Ala Ala Cys Phe Ser Leu Cys
1               5                   10                  15

Gly Pro Leu Leu Ser Ala Arg Thr Arg Ala Arg Arg Pro Glu Ser Lys
            20                  25                  30

Ala Thr Asn Ala Thr Leu Asp Pro Arg
        35                  40

<210> SEQ ID NO 2
<211> LENGTH: 41
<212> TYPE: PRT
<213> ORGANISM: Mus musculus

<400> SEQUENCE: 2

Met Gly Pro Arg Arg Leu Leu Ile Val Ala Leu Gly Leu Ser Leu Cys
1               5                   10                  15

Gly Pro Leu Leu Ser Ser Arg Val Pro Met Ser Gln Pro Glu Ser Glu
            20                  25                  30

Arg Thr Asp Ala Thr Val Asn Pro Arg
        35                  40

<210> SEQ ID NO 3
<211> LENGTH: 41
<212> TYPE: PRT
<213> ORGANISM: Artificial Sequence
<220> FEATURE:
<223> OTHER INFORMATION: scrambled synthetic human parstatin peptide

<400> SEQUENCE: 3

Leu Arg Thr Asn Ala Ser Leu Leu Val Pro Phe Leu Thr Ala Arg Ala
1               5                   10                  15

Lys Ser Ser Gly Thr Arg Glu Ala Ala Asp Pro Pro Arg Leu Met Cys
            20                  25                  30

Leu Arg Pro Leu Ala Arg Arg Cys Gly
        35                  40

<210> SEQ ID NO 4
<211> LENGTH: 18
<212> TYPE: PRT
<213> ORGANISM: Homo sapiens
```

<400> SEQUENCE: 4

Thr Arg Ala Arg Arg Pro Glu Ser Lys Ala Thr Asn Ala Thr Leu Asp
1               5                   10                  15

Pro Arg

<210> SEQ ID NO 5
<211> LENGTH: 41
<212> TYPE: PRT
<213> ORGANISM: Macaca mulatta

<400> SEQUENCE: 5

Met Gly Pro Arg Arg Leu Leu Val Ala Ala Cys Leu Cys Leu Cys
1               5                   10                  15

Gly Pro Leu Leu Ser Ala Arg Thr Arg Ala Arg Arg Pro Ala Ser Lys
            20                  25                  30

Ala Thr Asn Ala Thr Leu Asp Pro Arg
        35                  40

<210> SEQ ID NO 6
<211> LENGTH: 41
<212> TYPE: PRT
<213> ORGANISM: Rattus norvegicus

<400> SEQUENCE: 6

Met Gly Pro Arg Arg Leu Leu Val Ala Val Gly Leu Ser Leu Cys
1               5                   10                  15

Gly Pro Leu Leu Ser Ser Arg Val Pro Met Arg Gln Pro Glu Ser Glu
            20                  25                  30

Arg Met Tyr Ala Thr Pro Tyr Ala Thr
        35                  40

<210> SEQ ID NO 7
<211> LENGTH: 41
<212> TYPE: PRT
<213> ORGANISM: Cricetulus longicaudatus

<400> SEQUENCE: 7

Met Gly Pro Gln Arg Leu Leu Val Ala Ala Gly Leu Ser Leu Cys
1               5                   10                  15

Gly Pro Leu Leu Ser Ser Arg Val Pro Val Arg Gln Pro Glu Ser Glu
            20                  25                  30

Met Thr Asp Ala Thr Val Asn Pro Arg
        35                  40

<210> SEQ ID NO 8
<211> LENGTH: 41
<212> TYPE: PRT
<213> ORGANISM: Bos taurus

<400> SEQUENCE: 8

Met Gly Pro Arg Trp Leu Leu Leu Trp Ala Ala Gly Leu Gly Leu Cys
1               5                   10                  15

Ser Pro Leu Val Ser Ala Arg Thr Arg Gly Pro Arg Pro Gly Thr Asp
            20                  25                  30

Pro Thr Asn Gly Thr Leu Gly Pro Arg
        35                  40

<210> SEQ ID NO 9
<211> LENGTH: 6
<212> TYPE: PRT

```
<213> ORGANISM: Homo sapiens

<400> SEQUENCE: 9

Ser Phe Leu Leu Arg Asn
1               5

<210> SEQ ID NO 10
<211> LENGTH: 23
<212> TYPE: PRT
<213> ORGANISM: Homo sapiens

<400> SEQUENCE: 10

Met Gly Pro Arg Arg Leu Leu Leu Val Ala Ala Cys Phe Ser Leu Cys
1               5                   10                  15

Gly Pro Leu Leu Ser Ala Arg
            20
```